US010543293B2

(12) United States Patent
Suschek

(10) Patent No.: US 10,543,293 B2
(45) Date of Patent: Jan. 28, 2020

(54) MEDICAL DRESSING

(71) Applicant: BSN MEDICAL GMBH, Hamburg (DE)

(72) Inventor: Christoph V. Suschek, Langenfeld (DE)

(73) Assignee: BSN medical GmbH, Hamburg (DE)

( * ) Notice: Subject to any disclaimer, the term of this patent is extended or adjusted under 35 U.S.C. 154(b) by 436 days.

(21) Appl. No.: 15/034,159

(22) PCT Filed: Nov. 7, 2014

(86) PCT No.: PCT/EP2014/074029
§ 371 (c)(1),
(2) Date: May 3, 2016

(87) PCT Pub. No.: WO2015/067746
PCT Pub. Date: May 14, 2015

(65) Prior Publication Data
US 2016/0296655 A1    Oct. 13, 2016

(30) Foreign Application Priority Data

Nov. 7, 2013   (DE) .................... 10 2013 018 642

(51) Int. Cl.
| A61L 15/44 | (2006.01) |
| A61L 15/18 | (2006.01) |
| A61F 13/00 | (2006.01) |
| A61F 13/02 | (2006.01) |
| A61L 15/20 | (2006.01) |
| A61M 35/00 | (2006.01) |

(52) U.S. Cl.
CPC ........ *A61L 15/18* (2013.01); *A61F 13/00029* (2013.01); *A61F 13/00063* (2013.01); *A61F 13/02* (2013.01); *A61L 15/20* (2013.01); *A61L 15/44* (2013.01); *A61M 35/00* (2013.01); *A61L 2300/114* (2013.01); *A61M 2202/0275* (2013.01)

(58) Field of Classification Search
CPC ....... A61M 35/00; A61H 33/14; A61H 35/00; A61H 35/006; A61K 9/0009
See application file for complete search history.

(56) References Cited

U.S. PATENT DOCUMENTS

| 6,620,379 B1 * | 9/2003 | Piuk ................. A61K 33/40 422/292 |
| 2001/0056108 A1 * | 12/2001 | Lai .................. A61K 31/137 514/364 |
| 2009/0108777 A1 | 4/2009 | Hyde et al. |

(Continued)

FOREIGN PATENT DOCUMENTS

| CN | 1306423 A | 8/2001 |
| EP | 1903003 * | 3/2008 ............. C01B 21/24 |
| WO | 9966924 A1 | 12/1999 |

*Primary Examiner* — Kai H Weng
(74) *Attorney, Agent, or Firm* — Rankin, Hill & Clark LLP

(57) ABSTRACT

The present invention relates to a medical dressing that has a modular structure consisting of at least two layers and that is able to cleave incorporated photolabile nitric oxide donors in an adjoining absorption module by means of the emission of electromagnetic radiation from a light module, so that the photolytically generated nitric oxide can be used to enhance medical therapies in humans and animals as well as to generate NO.

22 Claims, 6 Drawing Sheets

(56) References Cited

U.S. PATENT DOCUMENTS

Figure 1:
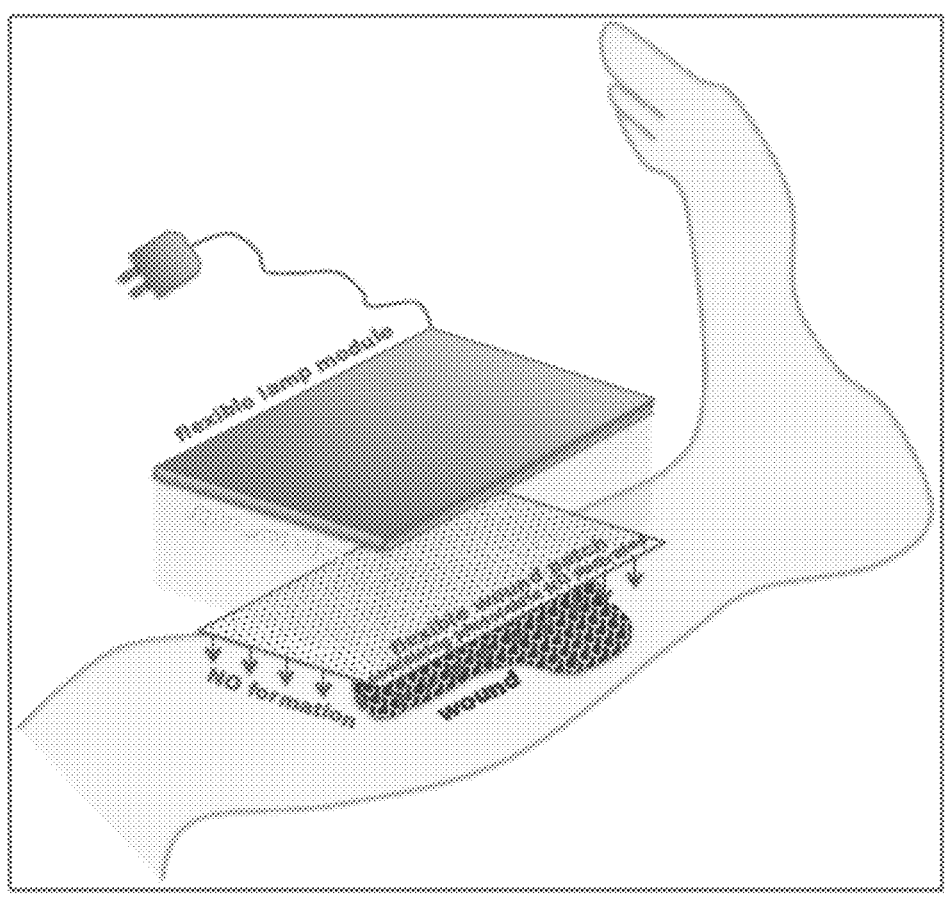

2011/0033437 A1    2/2011  Smith et al.
2011/0104240 A1*  5/2011  Jones ...................... A23B 4/16
                                                            424/443
2013/0330244 A1   12/2013  Balaban et al.

* cited by examiner

MEDICAL DRESSING

The present invention relates to an NO-releasing medical dressing. This dressing is modularly structured especially out of at least two layers and it is capable of cleaving photolabile nitric oxide donors that are incorporated in an adjacent, preferably closely adjoining, absorption module by means of the emission of electromagnetic radiation from a light module, so that the photolytically generated nitric oxide can be used to enhance medical therapies in humans and animals as well as in order to generate NO.

The treatment of impaired perfusion and of the resultant chronic wounds remains inadequate in day-to-day clinical practice. These ailments are not only a serious medical problem, but also an economic problem. For instance, it is estimated that, in Germany alone, some 2.4 million diabetics suffer from impaired perfusion and/or inadequate wound healing. This hampers the quality of life of those affected and they endure avoidable pain. The annual treatment costs are estimated at 3 billion euros. As the population ages, far more people will experience such poorly healing wounds in the future. In fact, estimates indicate that these numbers will have doubled by the year 2025.

Current therapeutic approaches are based primarily on the moderately effective pharmacological support of tissue perfusion as well as on insufficient support in the form of wound dressing systems for the healing of chronic wounds.

An important physiological principle of the human skin is the enzymatic production of nitric oxide by enzymes from the family of the NO synthases, which can be synthesized by all types of cells [1]. The substrate of the NO synthases is the amino acid L-arginine. A distinction is made nowadays between two constitutively expressed and one inducible isoform of the NO synthases. The constitutively expressed NO synthases include the primarily neuronally localized NO synthase (nNOS) and the primarily endothelially localized NO synthase (eNOS) which, however, is also expressed in dermal fibroblasts and in the musculocutaneous flap, whereas the inducible isoform, the iNOS, is only induced by the effect of proinflammatory stimuli and, in contrast to the constitutive isoforms, can produce locally high concentrations of NO over a prolonged period of time (days).

Below, the terms nitrogen monoxide, nitric oxide, nitric oxide radical, NO and NO. will be employed as equivalent terms for the same molecule.

In addition, NO can also be released non-enzymatically from nitrite or nitrosothiols. The non-enzymatic generation of NO takes place under acidic and reducing conditions. In this process, NO is released, for example, from nitrite. This reaction is physiologically significant in the acidic environment of the stomach as well as of the skin. It is also known that UVA light can release from nitrite a substance having the physiological properties of NO [2]. In fact, it has been demonstrated that NO can be formed from nitrite through the modality of photodecomposition [3; 4].

Within the scope of inflammatory processes of the skin and in an interaction of the various cell systems, NO regulates, among other things, the proliferation and the differentiation of skin cells and thus, for instance, also wound healing [5]. A number of genes have been identified as being dominantly NO-regulated in wound-healing processes of the skin [6; 7], and accordingly, wound healing in iNOS-deficient mice has been found to be a significantly delayed process [8]. Other genes that are under transcription control by NO are protectively active stress-protection genes such as heat-shock proteins, chaperones or also heme oxygenase-1. Other NO-regulated genes serve either to counter-regulate inflammatory reactions or to repair local damage (this especially includes many members of the family of matrix metalloproteinases (MMP)). NO can influence the gene expression of the MMPs, and also their physiological inhibitors, the tissue inhibitors of matrix proteinases (TIMP), and besides, NO can modulate their activity by means of nitrosation, thus countering greater collagen breakdown by the MMPs [9]. In addition, NO also influences the expression and activity of growth factors such as, for instance, VEGF [37; 38]. Thus, NO donors were able to stimulate, for example, angiogenesis which, along with collagen synthesis, is a key element in wound healing [39], whereby NO in keratinocytes and macrophages is capable of inducing the synthesis of the angiogenesis factor VEGF [5; 40].

Furthermore, experiments with exogenic NO donors have shown that NO leads to a significant increase in collagen synthesis in fibroblasts [10; 11]. An important physiological inductor of the synthesis of new collagen is the transforming growth factor-β (TGF-β), in contrast to which interleukin-1 (IL-1), IL-6, TNF-α as well as reactive oxygen species (ROS) can significantly reduce or even inhibit the synthesis of new collagen [12; 13]. Owing to its capability to react with other radicals and thus to eliminate them, NO can also have a protective effect [14]. For instance, NO is able to protect against DNA damage induced by hydroxyl radicals as well as against cell death induced by $H_2O_2$, and it also has a greater capacity than vitamin E to terminate radical-induced lipid peroxidation [15; 16].

In addition, numerous other protective properties of NO are described. Thus, NO is said to protect against hypoxia-induced damage, it develops hepatocyte-protective and neuro-protective effects and can also protect against apoptosis by inactivating effector caspases [17]. Moreover, already at low concentrations, NO can modulate important components of antioxidative protection such as, for example, glutathione metabolism (GSH) in that it induces an increase in the expression of the two key enzymes of GSH synthesis, namely, γ-glutamylcysteine synthetase (γ-GCS) and γ-glutamyl transpeptidase [18].

Once it has been formed, NO easily diffuses into the vessel wall as well as into the vessel lumen, and it is involved, for instance, in regulating thrombocyte adhesion and thrombocyte aggregation, vascular rolling and the transmigration of neutrophilic granulocytes and monocytes, as well as endothelial permeability [20]. NO also relaxes the smooth muscle cells in the vessel wall by activating soluble guanylate cyclase, the key enzyme in the regulation of blood pressure. Therefore, the endothelially formed NO is of essential significance for maintaining vascular function as well as vascular structure, thus essentially influencing hemodynamic parameters, especially blood pressure, but also tissue-ischemic conditions [21; 22].

In the case of a reduced NO synthesis rate, animal models have shown a delay in the formation of new vessels and in wound healing as well as a greatly impaired re-epithelization of skin wounds due to a reduced proliferation rate of the keratinocytes. As a transmitter of vascular relaxation, NO can increase the blood flow rate in the wound area, thus leading to a greater supply of oxygen and nutrients as well as to improved cellular infiltration of the tissue [5].

The topical treatment of wounds with NO donors during the early phase of cutaneous wound healing translates into a significantly accelerated wound closure and re-epithelization in rats [23] as well as into improved wound healing in mice with a diabetic background [24]. The daily topical exposure of wounds to air-plasma containing NO significantly improved wound healing of septic as well as aseptic wounds in rat models [25]. In spite of numerous indications of the positive effect of NO on wound healing, up until now, there has been only one documented pilot study in humans, namely, a study involving a 55 year-old patient in whom an NO gas therapy led to the complete healing of an *Ulcus cruris venosum* on the foot which had been resistant to therapy for several years [26]. Through the breakdown of reactive oxygen species, exogenically administered NO can diminish damage caused by ischemia or reperfusion and can considerably improve the microcirculation of skin tissue. These properties play a special role in the revitalization of edge zones of free skin flap plastic surgery within the scope of soft-tissue coverings [26].

Current therapeutic approaches relating to the NO balance primarily attempt to address the NO-induced cGMP-dependent signal cascade. Therapeutic approaches aimed at directly influencing NO availability in the organism are limited to the use of organic nitrites and nitrates [27]. In clinical practice so far, NO gas has only been employed as an inhalation therapy in the treatment of various acute pulmonary dysfunctions, whereby experimental studies have also demonstrated a systemic effect of inhaled NO [28]. The diffusion coefficient of NO at 37° C. [98.6° F.] is approximately 1.4 times higher than that of oxygen or carbon monoxide, on which basis the diffusion path that can be achieved in the tissues was calculated to be 500 µm [29].

Ghaffari et al. were able to demonstrate significant antibacterial effects and thus the relevance of exogenic NO gas in the treatment of bacteria-infected wounds and burn injuries as well as of non-healing wounds [31; 32], whereby the NO concentrations employed in vitro did not display any toxic effects on human fibroblasts, keratinocytes or endothelial cells [33].

In summary, nitric oxide (NO) has proven to be a physiologically important bioactive molecule. Owing to its dilating effect on blood vessels, which sets in very rapidly, NO is of great significance for the supply of blood to the organs. Moreover, NO also plays a role as an important messenger substance in other physiological processes. For instance, as a radical trap, NO protects against hypoxia-induced damage and it modulates important components of antioxidative protection. Remarkably, in case of inflammatory processes of the skin, in an interaction with the various cell systems, for example, NO regulates the proliferation and differentiation of skin cells, thus promoting wound healing.

Correspondingly, it has been found in animal models that a reduced NO synthesis rate is associated with a delayed formation of new vessels and with wound healing.

On the basis of these insights pertaining to NO, there are already approaches to use gaseous NO for the therapy of impaired perfusion or chronic wounds. Up until now, NO-containing gas used for therapeutic purposes has been supplied in gas cylinders (industrial gas), as a result of which its storage and handling in a hospital or in another therapeutic institution are demanding in view of the requisite safety measures. This applies especially to a mobile device. Moreover, the quality of the stored gas used for medical applications has to meet strict requirements, and this further increases the demands made in terms of its production and storage. Even a slight contamination of the gas leads to the formation of undesired and conceivably toxic byproducts. Accordingly, European drug and health authorities have laid down strict requirements pertaining to the purity of the nitric oxide to be used. Aside from the use of "technical" NO gases for medical applications, there are methods for the plasma-chemical production of nitric oxide. These methods require subsequent, sometimes very demanding, purification procedures, and it is difficult to set the optimal concentration of NO for the therapeutic objective in question.

Consequently, there is still a need for new methods for treating impaired perfusion and chronic wounds.

Before this backdrop, the objective of the invention is to put forward a new therapeutic approach for treating impaired perfusion and chronic wounds which is improved with respect to at least one of the above-mentioned drawbacks.

SUMMARY OF THE INVENTION

This objective is achieved according to the invention in that a medical dressing is put forward that comprises the following:
  a. a radiation-emitting module having a source of radiation for the emission of electromagnetic radiation, and
  b. an NO module (NOM) containing photolabile nitric oxide donors (NOD), whereby the electromagnetic radiation stemming from the radiation-emitting module can cleave these nitric oxide donors, so that the NO module generates NO that can then be released from the NO module;
  whereby in the dressing, a system is used that degrades or neutralizes polyoxidized nitrogen oxides, oxygen radical anions, hydroxyl radicals or hydrated electrons.

Thus, according to the invention, the medical dressing comprises:
  a. a radiation-emitting module having a source of radiation for the emission of electromagnetic radiation, and
  b. an NO module (NOM) containing photolabile nitric oxide donors (NOD), whereby the electromagnetic radiation stemming from the radiation-emitting module can cleave these nitric oxide donors, so that the NO module generates NO that can then be released from the NO module;
  c. a system that degrades or neutralizes polyoxidized nitrogen oxides, oxygen radical anions, hydroxyl radicals or hydrated electrons.

The medical dressing according to the invention combines several decisive advantages in comparison to the therapeutic approaches known from the state of the art.

In a surprising manner, it has been found that, within the scope of such a medical dressing, NO that is free of impurities and that is thus suitable for medical applications can be produced in a reliable manner by means of a system that degrades or neutralizes polyoxidized nitrogen oxides, oxygen radical anions, hydroxyl radicals or hydrated electrons (also referred to as a "radical trapping system" within the scope of the invention).

The medical dressing permits the transdermal administration of NO, which is associated with numerous advantages; in particular, gastrointestinal incompatibility and a hepatic first-pass effect are avoided.

Moreover, the vasodilatation of the skin microcirculation induced by NO can significantly increase the percutaneous absorption of pharmacologically active substances. In this context, the NO acts as a penetration promoter or transport mediator.

Even though physiologically relevant NO concentrations can be generated in the NO module that serves as an absorption module, due to the limited dissolving behavior of NO, these concentrations are far below those that could cause harm to the health of humans.

Moreover, through direct contact of the surface of the human body with the photolytically generated nitric oxide-releasing module of the device, a much more accurate NO treatment can be achieved than, for example, with gas mixtures containing NO or with spontaneously disintegrating NO donors.

Normally, the short half-life of NO hampers its therapeutic use. With the device according to the invention, despite the short half-life, a constant NO level can be maintained, thanks to a continuous NO after-synthesis.

This regulation and control capability is a decisive advantage, precisely in the therapeutic realm, since it allows treatment that is tailored to a given patient.

The modular structure of the medical dressing also permits the use of a module containing nitric oxide donors as a replaceable disposable article, which can ensure a reproducible and reliable production of NO.

A simple adaptation of the NO module in terms of its size, shape and material can adapt the medical dressing to the treatment requirements in a targeted manner.

Thus, by using NO-impermeable layers, here especially a backing layer or adhesive layers on the edges, the NO can be applied to the exposed skin region in a targeted manner and consequently does not escape into the surroundings.

Since the NO-generating module is a component of the medical dressing according to the invention, it is possible to dispense with an external supply of NO, which usually involves gas cylinders.

This permits its utilization as a mobile system which, precisely in the therapeutic realm, allows its use outside of doctor's offices and clinics, and therefore translates into a more cost-efficient treatment and greater patient compliance, particularly in the case of chronic diseases.

The dressing according to the invention is a simply structured medical dressing made up of commercially available components, so that it is not only cost-effective to produce but also easy to use while not being prone to causing errors during use.

In summary, the dressing according to the invention constitutes an NO-based therapy modality with which NO can be released by a medical dressing in a manner that is inexpensive, reliable, safe and individualized for the patient.

THE INVENTION IN DETAIL

In a second aspect, the invention puts forward a medical dressing comprising an NO module (NOM) containing photolabile nitric oxide donors (NOD), whereby electromagnetic radiation can cleave these nitric oxide donors, so that the NO module generates NO that can then be released from the NO module. Here, the NO module comprises a system that degrades or neutralizes polyoxidized nitrogen oxides, oxygen radical anions or hydroxyl radicals (radical trapping system).

In a third aspect, the invention puts forward a medical dressing comprising an NO module (NOM) containing photolabile nitric oxide donors (NOD), whereby the NO module additionally contains transition metal cations (so-called NO-active transition metal cations) that can release the NO through reduction from the nitric oxide donors.

Within the scope of the present invention, the term transition metals refers to the chemical elements having the atomic numbers from 21 to 30, 39 to 48, 57 to 80 and 89 to 112.

It has been found that, in case of radiation-induced NO generation by the NO-active transition metal cations that are present, NO can be generated in a far greater yield in the medical dressing, and the formation of reactive oxygen species and of more highly oxidized nitrogen oxide species does not take place, so that the NO obtained is of high purity. Consequently, in this aspect of the invention, the radical trapping system can be dispensed with in the medical dressing.

Moreover, it has been found that these transition metal cations can already release the NO through the mere reduction of the NO donor, even without electromagnetic radiation. Therefore, on the one hand, during the administration, the source of radiation can be dispensed with, while on the other hand, this means that the two reaction components, that is to say, the NO-active transition metal cations and the nitric oxide donors, are only allowed to come together at the time of the administration. For this purpose, various embodiments are possible:

The NO-active transition metal cation is produced in situ from an inactive valence stage of the corresponding cation by means of reduction or oxidation. Here, it must be ensured that the redox reaction only takes place at the time of the administration. This can be ensured by separating the redox agent from the inactive cation, whereby, during the administration, the reaction is started by mixing the components. As an alternative, the NO-active transition metal cation and the nitric oxide donors can be present in the NO module separately from each other.

In a preferred embodiment, the NO-active transition metal cation is produced by a light-induced redox reaction in the NO module.

In one embodiment, the NO-active transition metal cation is a low-valence cation, that is to say, there is also a higher-valence cation for the corresponding cation.

Here, these two valences of the transition metal cation form a redox pair, whereby the low-valence cation is converted into the higher-valence cation during the reduction of the NO donor. Thus, these two cations form the redox pair of an NO-generating reaction, which can be formulated as follows:

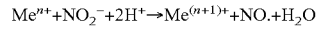
$$Me^{n+}+NO_2^-+2H^+ \rightarrow Me^{(n+1)+}+NO.+H_2O$$

Preferably, $Fe^{2+}$, $Co^+$, $Ru^{2+}$ or $Cu^+$ are used as the cations. They can be present in the NO module in the form of organic or inorganic salts.

In a preferred manner, nitrites or S-nitrosothiols are used as the nitric oxide donors for the reaction with the transition metal cations. A corresponding reaction of $Cu^+$ with nitrite takes place as follows:

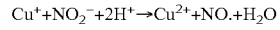
$$Cu^++NO_2^-+2H^+ \rightarrow Cu^{2+}+NO.+H_2O$$

Since the low-valence cation is consumed along with the associated NO generation during this redox reaction, it is advantageous to either have a surplus of this cation or to generate it again by means of reduction.

In a preferred embodiment, in addition to the transition metal cation, the NO module contains a reductant for regenerating this metal cation.

In one embodiment, the reductant is the radical trapping system. Thus, substances such as ascorbate, vitamin or glutathione can reduce the higher-valence transition metal cation into a low-valence cation.

In a preferred embodiment, the nitric oxide donors themselves are used as the reductants, whereby, under the effect of electromagnetic radiation, the nitric oxide donors reduce the higher-valence transition metal cation into a low-valence cation.

Thus, together with nitrite or S-nitrosothiols, the Cu' cation is able to form a nitrite triplet complex whereby, under radiation with light ranging from 400 nm to 470 nm, preferably from 400 nm to 450 nm, the nitrite anion is oxidized to form $NO_2$ and the $Cu^{2+}$ is reduced to form $Cu^+$.

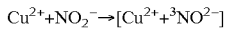

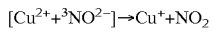

The Cu(I) cation obtained in this manner can then release the NO through reduction of a nitrite anion, whereby here, too, the NO is of high purity, that is to say, it has a purity that is prescribed for therapeutic use.

Accordingly, in a special embodiment, the invention provides a medical dressing that comprises an NO module (NOM) containing the photolabile nitric oxide donors (NOD) and $Cu^{2+}$ cations, whereby, through radiation with light having a wavelength ranging from 400 nm to 470 nm, preferably between 400 nm and 450 nm, NO is generated in the NO module by reduction of the NO donors and this NO can then be released from the NO module.

Since no harmful by-products are formed in the case of this special form of light-induced NO release, it is possible to dispense with the radical trapping system here as well.

In a special embodiment, the transition metal cation is a Cu' ion. It can be reduced by light within the range from 400 nm to 470 nm (blue light), a process in which complex formation occurs with a reductant to form Cu', whereby the reductant is oxidized. The $Cu^{1+}$ is then able to release the NO from the nitric oxide donor, especially from the nitrite, by means of a redox reaction. Accordingly, the use of $Cu(NO_2)_2$ is preferred here.

In one embodiment, the radical trapping system can be used as the reductant.

In a special embodiment, the NO module is configured as a multi-layered dressing. This multi-layered dressing of the present invention comprises (i) a layer containing nitric oxide donors (also "middle layer") in which the at least one photolabile nitric oxide donor is present in dissolved or suspended form, and (ii) an inner layer that is permeable to NO ("inner layer"), as well as (iii), if applicable, a protective film and/or a backing layer.

In an advantageous embodiment, the multi-layered NO module also comprises an outer layer ("outer layer"). In this context, the outer layer is one that directly or indirectly adjoins the middle layer containing the nitric oxide donor on the side facing away from the skin.

The outer layer can preferably be arranged between the middle layer and the backing layer. According to one embodiment, the outer layer is essentially impermeable to NO. It can be self-adhesive or not self-adhesive. If it is not self-adhesive, adhesives can be provided in order to adhesively bond the outer layer to the backing layer.

Within the scope of the invention, the term "dressing" refers to any flat means that can be placed onto regions of the body. Here, the placement comprises a simple placement without close or adhesive contact, or else an at least partially adhesive bond of the dressing with the skin. Such an adhesive bond or glued bond is advantageously configured as a reversible adhesive bond.

The middle layer of the NO module is characterized in that it contains one or more photolabile nitric oxide donors (NOD). In a preferred manner, it also contains a radical trapping system.

The employed substances of the radical trapping system not only capture the radical by-products that are formed during the NO generation, but they also ensure that the appertaining layer is low in oxygen or even free of oxygen, thereby preventing even an initial reaction of the formed NO with the oxygen.

In an advantageous manner, the photolabile nitric oxide donors and the radical trapping system are present in the same layer. As a result, the radicals that are formed as by-products during the photolysis can be trapped directly, without their reacting with other substances and forming possibly toxic substances. Preferably, the nitric oxide donors and the radical trapping system are present in the middle layer.

In an alternative embodiment, for example, in case of a chemical incompatibility of the nitric oxide donor and the radical trapping system, these two components are present in different layers. Here, it is advantageous for the nitric oxide donor to be present in the middle layer and for the radical trapping system to be present in the inner layer, so that the NO, which, together with its by-products, has been generated by photolysis, is purified before reaching the skin as it passes through the inner layer.

The "radical trapping system" of the above-mentioned embodiment is preferably an anti-oxidant and especially preferably ascorbate or ascorbic acid.

Here, the concentration of the radical trapping system relative to the total weight of the layer(s) containing it can be up to 20% by weight, preferably between 0.25% and 10% by weight, especially preferably between 3% and 7.5% by weight.

In a preferred embodiment of the invention, the photolabile nitric oxide donors (NOD) of the NO module are selected from the group containing organic nitrates, inorganic nitrates, nitrites, sulfur-nitroso, nitrogen-nitroso or oxygen-nitroso compounds, NO-metal compounds and NO-chelating substances.

Photolabile nitric oxide donors are known in the state of the art and are familiar to the person skilled in the art.

Examples of photolabile nitric oxide donors include diazeniumdiolates (for example, U.S. Pat. Nos. 7,105,502; 7,122,529; 6,673,338), trans[RuCl([15]aneN$_4$)NO]$^{+2}$, nitrosyl-ligands, 6-nitrobenzo[a]pyrrole, S-nitrosoglutathione, S-nitrosothiol, nitroaniline derivates (see U.S. Pat. Appln. No. 2013/0224083), 2-methyl-2-nitrosopropane, imidazoyl derivates, hydroxylnitrosamine, hydroxylamine and hydroxy urea.

In another embodiment, the NO module and preferably its layer or layers containing nitric oxide donors have a content of NO donors between 0.1% and 50% by weight, preferably between 0.25% and 20% by weight, particularly preferably between 0.5% and 10% by weight, and especially between 2.5% and 7.5% by weight, relative to the total weight of the layer(s) containing them.

In a preferred manner, the nitric oxide donors are pharmacologically compatible substances. These include, for example, nitrites of alkali or earth alkali metals.

The following are mentioned here by way of example: $LiNO_2$, $NaNO_2$, $KNO_2$, $RbNO_2$, $CsNO_2$, $FrNO_2$, $Be(NO_2)_2$, $Mg(NO_2)_2$, $Ca(NO_2)_2$, $Sr(NO_2)_2$, $Ba(NO_2)_2$ or $Ra(NO_2)_2$.

Special preference is given here to $NaNO_2$ as the nitric oxide donor that, in a likewise preferred manner, is contained in the medical dressing along with ascorbate or ascorbic acid as the radical trapping system.

The concentration of the nitrite salts relative to the total weight of the layer(s) containing them can be up to 20% by weight here, preferably between 0.25% and 10% by weight, especially preferably between 3% and 7.5% by weight.

In another embodiment of the invention, the nitric oxide donors can be coupled to a polymer. Appropriate methods for coupling nitric oxide donors to polymers are disclosed, for example, in U.S. Pat. No. 5,405,919. In one embodiment, the nitric oxide donor-coupled polymer is a polymer that is provided with diazoniumdiolate groups. An example of this is linear polyethylenimine (PEI) derivatized with diazoniumdiolate groups, which is disclosed in international patent application WO 2006/058318 A2.

The concentration of generated NO in the NOM is between 10 µM and 5 mM, preferably between 100 µM and 3 mM, and especially preferably between 150 µM and 2 mM.

The quantity of released NO is between 50 ppm and 600 ppm, and preferably between 160 ppm and 400 ppm. Such quantities are therapeutically effective without causing severe side effects.

The person skilled in the art is familiar with numerous systems that are able to degrade or neutralize polyoxidized nitrogen oxides, oxygen radical anions, hydroxyl radicals or hydrated electrons. He or she will select them as a function of the layer composition of the NO module.

In one embodiment, the radical trapping system is present in the layer containing nitric oxide donors so that it can directly degrade or neutralize the oxidized nitrogen oxides, oxygen radical anions, hydroxyl radicals or hydrated electrons that arise during the NO formation.

As an alternative, the radical trapping system can also be present in the inner layer so that, when the NO passes through this layer facing the skin, it can degrade or neutralize the oxidized nitrogen oxides, oxygen radical anions, hydroxyl radicals or hydrated electrons that arise during the NO formation.

Moreover, the possibility exists that the middle layer as well as the inner layer can contain the radical trapping system.

Suitable antioxidants for a lipophilic NO module layer, that is to say, a layer with hydrophobic polymers of the kind that can be provided by a hydrophobic polymer, include, for instance, the following: tocopherols, tocotrienols, tocomonoenols, Irganox®, Irgafos®, butylated hydroxyanisole (BHA) and butylated hydroxytoluene (BHT).

Organic compounds containing sulfur such as, for example, glutathione, cysteine or thiolactic acid, or else organic acids such as ascorbic acid, alpha-liponic acid, hydroxy cinnamic acids such as p-cumaric acid, ferulic acid, sinapinic acid or caffeic acid, or hydroxybenzoic acids such as gallic acid, protocatechuic acid, syringic acid or vanillic acid are especially suitable for a hydrophilic NO module layer, that is to say, a layer with hydrophilic polymers.

Other preferred antioxidants include polyphenolic compounds such as anthocyane, flavonoids and phytoestrogens.

In a preferred manner, the NO module, and here preferably also the middle layer, contains one or more of the following substances: catalysts, detergents, buffering substances, chromophores, substances that stabilize the nitric oxide donor such as, for example, dimethyl sulfoxide or ethanol, substances that increase the half-life of NO such as those described, for example, in U.S. Pat. Appln. No. 2003/0039697, nitric oxide donor stabilizers, antioxidants, dyes, pH indicators, care products, fragrances, and pharmacologically active substances.

In another preferred embodiment, the multi-layered NO module, and here preferably the middle layer, also contains a crystallization inhibitor. Various surfactants or amphiphilic substances can be used as crystallization inhibitors. They should be pharmaceutically acceptable and approved for use in drugs. An especially preferred example of such a crystallization inhibitor is soluble polyvinylpyrrolidone, which is commercially available, for example, under the brand name Kollidon® (Bayer AG). Other suitable crystallization inhibitors contain copolymers of polyvinylpyrrolidone and vinyl acetate, polyethylene glycol, polypropylene glycol, glycerol and fatty acid esters of glycerol or copolymers of ethylene and vinyl acetate.

Optionally, the NO module contains a penetration promoter. Such penetration promoters (also called permeation enhancers) improve the permeation properties for the penetration of the pharmacologically active substances into the skin. Examples of penetration promoters are, among other things, fatty alcohols, fatty acids, fatty acid esters, fatty acid amides, glycerin or glycerin fatty acid esters, N-methyl pyrrolidone, terpenes such as limonene, α-pinene, α-terpineol, carvone, carveol, limonene oxide, pinene oxide or 1,8-eucalyptol.

On the basis of the general technical expertise of the person skilled in the art, he/she will select suitable substances or substance mixtures with an eye towards the envisaged application. In this context, he/she will especially take into consideration the fact that physiologically compatible and/or dermatologically compatible substances and substance mixtures will be employed when the invention is used as a medical dressing.

In one embodiment of the invention, the medical dressing, and here especially the inner and/or middle layer, contains one or more pharmacologically active substances. These substances can support the pharmacological effect of the NO or else can have a therapeutically relevant effect on a given disease, independently of the NO.

In one embodiment of the invention, the medical dressing contains one or more of the following pharmacologically active substances: anti-inflammatory agents such as, for instance, nonsteroidal anti-inflammatory drugs (NSAIDs) or corticoids, immunosuppressants, antibiotics, anticoagulants, antithrombotic agents, antiviral agents, antimycotic agents, local anesthetics and analgesics.

In a preferred embodiment, the pharmacologically active substance is present in the form of wax-like particles that have a low melting point and that melt upon contact with the skin, thereby releasing the substance.

The pH value of the middle and/or inner layer is advantageously between 3.0 and 10, preferably between 5.5 and 7.4, and especially preferably between 6.0 and 7.0.

In another embodiment, the NO module, and here preferably the layer containing nitric oxide donors, is low in oxygen or free of oxygen. Accordingly, the oxygen content of the NO module or of the layer containing nitric oxide donors is less than 20 ppm, preferably less than 10 ppm, especially preferably less than 5 ppm.

The low level or absence of oxygen according to the invention can be brought about by treating the individual components of the NO module or by gassing intermediate stages or the finished NO module with an inert gas (such as, for instance, argon or nitrogen). Such an NO module should advantageously be packed gas-tight so that the low level or absence of oxygen is retained until the point in time of use.

In another embodiment, the NO module, and here preferably the layer(s) containing nitric oxide donors, has an oxygen absorber in order to achieve the low level or absence of oxygen. Suitable oxygen absorbers include: Irganox®, Irgafos®, butylated hydroxyanisole, butylated hydroxytoluene, ascorbic acid or pyrogallol.

The layer containing nitric oxide donors advantageously has a weight per unit area of 70 $g/m^2$ at the most, preferably of 40 $g/m^2$ at the most, and especially preferably of 30 $g/m^2$ at the most.

A low weight per unit area on the part of the layer containing nitric oxide donors is advantageous since, in this manner, the NO module can deform in accordance with the microscopic bending movements of the skin.

The inner layer preferably has a weight per unit area of 15 g/m² to 55 g/m², preferably of 15 g/m² to 40 g/m², particularly preferably of 15 g/m² to 30 g/m², and especially from 15 g/m² to 25 g/m².

The outer layer preferably has a weight per unit area of 5 g/m² to 40 g/m², preferably of 5 g/m² to 30 g/m², particularly preferably of 5 g/m² to 25 g/m², and especially from 5 g/m² to 15 g/m².

A low weight per unit area of the inner layer and/or of the outer layer is advantageous since, as the layer thickness decreases, the tendency towards a cold flow also decreases. However, it should be kept in mind here that the thickness of the inner layer also has to ensure sufficient adhesion to the skin. Consequently, the inner layer preferably has a weight per unit area of at least 15 g/m², especially preferably even of at least 20 g/m².

In one embodiment, all of the layers have an identical weight per unit area of 20 g/m² to 40 g/m², preferably of 30 g/m². In a preferred embodiment, the weight per unit area of the layer containing nitric oxide donors is 30 g/m².

In an especially preferred embodiment, the weight per unit area of the outer layer is 10 g/m², of the middle layer containing nitric oxide donors is 30 g/m², and of the inner layer is 20 g/m². Thus, the weight per unit area amounts to a total of 60 g/m².

In one embodiment, the multi-layered NO module without the backing layer and protective film has a weight per unit area of 120 g/m² at the maximum, preferably of 90 g/m² at the maximum, particularly of 75 g/m² at the maximum, and especially preferably of 60 g/m² at the maximum.

The layers of the NO module are preferably configured as flexible layers so that they can establish a full-surface, close contact with the skin. The person skilled in the art is familiar with numerous methods and processes for producing flexible layers, for example, from U.S. Pat. Nos. 6,639,007, 6,673,871 or 7,105,607.

Advantageously, the layer facing the radiation-emitting module has a section that is permeable to UV radiation. Therefore, this is an activation window.

In another embodiment, the shape of the NO module is adapted to the part of the body that is to be treated. Thus, for example, it can be configured as a stocking, a sock, a bandage, a cuff, a glove or a finger wrap.

Therefore, the NO module should preferably be made of a material that does not affect the properties of the energy that stems from an electromagnetic source of radiation and that is needed for an optimal release of nitric oxide or that, due to its properties, actually creates or optimizes the light properties needed for a light-induced release of nitric oxide.

Advantageously, the NO module, and here especially the outer and/or middle layer, is permeable to UV radiation. Since the person skilled in the art knows about the UV permeability, he or she will select the right materials for the container that holds the carrier medium. Thus, it is advantageous to use UV-permeable plastics. Examples of these are polymethylpentene (PMP), modified polymethyl methacrylate (PMMA) or modified polyvinyl butyral (Trosivol UV+®).

In a preferred embodiment, the inner layer facing the skin is not permeable to the UV radiation, so as to protect the skin against a possibly damaging dose of UV radiation.

In one embodiment, the middle layer containing nitric oxide donors contains at least one hygroscopic polymer or copolymer (referred to below as "hygroscopic (co)polymer"). The at least one hygroscopic (co)polymer is preferably polyvinylpyrrolidone (PVP), polyvinyl alcohol (PVA), poly(vinyl pyrrolidone-co-vinyl acetate) or a carbohydrate polymer or a mixture or a copolymer thereof. Here, preferred carbohydrate polymers are cellulose or derivatives thereof, starch or derivatives thereof, alginates and pullulan. The cellulose and starch derivatives are preferably water-soluble.

Special preference is given to PVP, PVA as well as mixtures or copolymers thereof. Very special preference is given to PVP.

Preferably, PVP is used that has a mass average molar mass Mw of 20,000 to 3,000,000 g/mol, preferably of 100,000 to 2,500,000 g/mol, further preferred of 500,000 to 2,000,000 g/mol and especially preferably of 1,000,000 to 1,500,000 g/mol.

Preferably, PVA is used that has a mass average molar mass Mw of 5,000 to 100,000 g/mol, preferably of 10,000 to 50,000 g/mol, further preferred of 20,000 to 40,000 g/mol, and especially preferably approximately 31,000 g/mol.

The mean degree of polymerization DP of the PVA employed is preferably between 100 and 2050, preferably between 200 and 1025, further preferred between 400 and 825, and especially preferably about 630.

The degree of hydrolysis (saponification) of the PVA is between 75 mol-% and 100 mol-%, preferably between 80 mol-% and 95 mol-%, and further preferred between 85 mol-% and 90 mol-%.

It is possible to use, for example, PVP from the Kollidon product line made by BASF, especially Kollidon 90 F, as well as PVA from the Mowiol product line made by Clariant, especially Mowiol 4-88.

In an alternative embodiment, the middle layer containing nitric oxide donors contains at least one hydrophobic polymer. Examples of suitable hydrophobic polymers are polytetrafluoroethylene or polytrifluorochloroethylene.

The middle layer can consist, for example, essentially of fibers, whereby they can be configured as a fabric or as a nonwoven.

In one embodiment, the inner layer is configured as a self-adhesive matrix. It preferably has an adequate solubility and permeability for the nitric oxide. Preferably, it is impermeable to the NO donor.

The term "NO-permeable" as set forth in the present invention refers to a layer that is permeable to NO under the administration conditions, in other words, under the conditions on the skin of the patient.

The inner layer can have, for instance, one or more NO-permeable membranes. Such membranes are disclosed, for example, in U.S. Pat. Appln. No. 2002/0026937. In a preferred embodiment, the membrane is a selectively permeable membrane of the type produced, for example, by a copolymer consisting of 70% polyester and 30% polyether (e.g. Sipatex™, 10-µm membrane, see Hardwick et al., Clinical Science 100: 395-400 (2001)).

Moreover, the inner layer can also be applied as an NO-permeable coating onto the middle layer. Such NO-permeable coatings are known from U.S. Pat. Appln. Nos. 2003/0093143 A or 2005/0220838.

The self-adhesive matrix as the inner layer can preferably comprise a solid or semi-solid semi-permeable polymer, preferably a pressure-sensitive adhesive (glue, PSA) or a mixture of such adhesives. The pressure-sensitive adhesive(s) or glue(s) form(s) the matrix into which, if applicable, additional auxiliaries or additives are incorporated.

The adhesive is preferably pharmaceutically acceptable in the sense that it is biocompatible, non-sensitizing and nonirritating vis-à-vis the skin. Especially advantageous adhesives for use in the present invention should also meet the following requirements:
1. constant adhesive and co-adhesive properties when exposed to moisture or perspiration under normal temperature fluctuations,
2. good compatibility with NO, nitric oxide donors and other auxiliaries that are used in the formulation of the dressing.

Although different types of adhesives that react sensitively to pressure can be used in the present invention, preference is given to the use of hydrophobic adhesives that have a low absorption capacity for active ingredients as well as for water.

In one embodiment, the inner layer has at least one hydrophobic polymer. The at least one hydrophobic polymer can preferably be a polyisobutylene (PIB) or a mixture of different polyisobutylenes (PIBs), polybutylene, butyl rubber, a styrene copolymer, a styrene-butadiene-styrene block copolymer, a styrene-isoprene copolymer, a styrene isoprene, a silicon polymer or a mixture of different silicon polymers, ethylene vinyl acetate copolymers (EVA) or a mixture or a copolymer thereof.

Special preference is given to a PIB, a mixture of different PIBs, a silicon polymer, as well as a mixture of different silicon polymers. Very special preference is given to a PIB as well as to a mixture of various PIBs.

According to one embodiment, a PIB with a higher molecular weight is used.

The PIB with a higher molecular weight preferably has a mass average molar mass Mw of 100,000 to 1,000,000 g/mol, preferably of 150,000 to 800,000 g/mol, further preferred of 200,000 to 700,000 g/mol and especially preferably of 250,000 to 600,000 g/mol.

For example, a PIB with a Mw of approximately 250,000 g/mol or a PIB with a Mw of approximately 600,000 g/mol can be used.

According to another embodiment, a mixture of two PIBs having different molecular weights can be used. Preferably, a mixture of a PIB having a higher molecular weight and a PIB having a lower molecular weight can be used.

The PIB having the lower molecular weight preferably has a mass average molar mass Mw of 10,000 to 100,000 g/mol, preferably of 20,000 to 50,000 g/mol, further preferred of 30,000 to 40,000 g/mol and especially preferably of approximately 36,000 g/mol.

Advantageously, a low-molecular-weight polybutylene is added to this mixture. It is possible to use, for example, PIBs from the Oppanol product line made by BASF, and/or from the Durotak product line made by Henkel. Examples in this context are Oppanol 10, Oppanol 100, Oppanol 200, Durotak 87-6908 and Durotak 618a. However, the PIBs of the Durotak product line can also be easily admixed by persons skilled in the art themselves, for example, using those of the Oppanol product line such as B100, B10, etc.

Preferably, the silicon polymers used in the inner layer of the medical dressing are of the type that form a soluble polycondensed polydimethylsiloxane (PDMS) resin network, whereby the hydroxy groups are capped, for example, with trimethylsilyl (TMS) groups. Preferably, the weight ratio of resin to PDMS is 85:15 to 35:65, preferably 75:25 to 45:55 and especially preferably 65:35 to 55:45. Preferred silicon polymers of this type are BIO-PSA pressure-sensitive silicon adhesives which are made by Dow Corning, especially 07-420x and 07-430x grades, wherein the x stands for a manufacturer numerical code that characterizes the solvent employed in the adhesive in question (x=1: heptane, x=2: ethylacetate, x=3: toluene). However, it is also possible to use other silicon adhesives. BIO-PSA 07-420x, with its resin-to-PDMS weight ratio of 65:35, exhibits medium adhesiveness, whereas BIO-PSA 07-430x, with its resin-to-PDMS weight ratio of 55:45 exhibits high adhesiveness.

In another especially preferred aspect, two or more silicon adhesives are used as the main adhesive components. It can be advantageous for such a mixture of silicon adhesives to contain a mixture of highly adhesive, pressure-sensitive adhesives containing PDMS with a resin (e.g. 07-430x) as well as with medium-adhesive, pressure-sensitive silicon adhesives containing PDMS, along with a resin (e.g. 07-420x).

Such a mixture comprising a pressure-sensitive silicon adhesive that has a high and a medium adhesiveness as well as PDMS with a resin is advantageous since it entails an optimal balance between good adhesion and a low cold flow. An excessive cold flow can result in a dressing that is too soft and that can easily stick to the packaging or to the clothing of the patient. Moreover, such a mixture can be particularly useful in order to obtain a higher plasma level. Consequently, a mixture of the above-mentioned 07-420x (medium adhesiveness) and 07-430x (high adhesiveness) is especially useful for the medical dressing according to the present invention. Here, preference is given to mixing ratios of 1:50 to 50:1, especially preferably of 1:10 to 10:1 and especially of 1:1, between the medium-adhesive silicon adhesive and the high-adhesive silicon adhesive.

It is also possible for the above-mentioned hydrophobic polymers and copolymers to contain additional hydrophilic monomers, whereby the fraction of these hydrophilic monomers is 50 mol-% at the maximum, preferably 30 mol-% at the maximum, especially preferably 10 mol-% at the maximum.

In another aspect of the invention, "SxS pressure-sensitive adhesives" are used for the inner layer. SxS pressure-sensitive adhesives are styrene block copolymer-based adhesives that have non-elastomer styrene bridges at the ends and elastomer blocks in the middle. The elastomer blocks can consist, for example, of polyethylene butylene, polyethylene propylene, polybutadiene, polyisobutylene or polyisopropene.

Suitable SxS adhesives are described, for instance, in U.S. Pat. Nos. 5,559,165 and 5,527,536, and they are characterized by good adhesive properties, simple production and processing as well as good skin compatibility.

SxS pressure-sensitive adhesives can be purchased commercially (for example, as Duro Tak 378-3500 from National Starch & Chemical) and can also be made with hot-melt extrusion equipment during the production of the multi-layered NO module. For this purpose, for example, appropriate amounts (of at least the following components) of a styrene block copolymer (e.g. Shell Kraton GX1657 or Kraton D-1107CU) with an aliphatic and/or aromatic resin (e.g. Keyser Mackay Regalite R1090 or Regalite R1010 or Regalite R1100) and an oil (e.g. Shell Ondina 933 or Ondina 941) are metered from their individual metering stations into the extruder, mixed there and melted. In the last step, the active ingredient is metered into the pressure-sensitive adhesive produced in this manner and the compound is laminated onto sheets. Typical examples of the parts by weight of polymer-to-resin-to-oil are ratios, for instance, of 100:120:20 or 100:200:50. By varying these fractions, the properties of the SxS pressure-sensitive adhesive can be adapted to the specifically desired properties of the medical dressing (adhesive force, minimal cold flow, adhesive duration, release profile of the active ingredient, etc.).

Advantageous combinations of polymers of the middle and inner layers are listed in the table below:

In this table, the definitions are as follows:

"TH-PVA": partially hydrolyzed polyvinyl alcohol. Preferred examples of TH-PVAs are Mowiol 3-85, Mowiol 4-88, Mowiol 5-88, Mowiol 8-88, Mowiol 13-88, Mowiol 18-88, Mowiol 23-88, Mowiol 26-88, Mowiol 32-88, Mowiol 40-88, Mowiol 47-88 and Mowiol 30-92.

"VH-PVA": completely hydrolyzed polyvinyl alcohol. Preferred examples of TH-PVAs are Mowiol 4-98, Mowiol 6-98, Mowiol 10-98, Mowiol 20-98, Mowiol 30-98, Mowiol 56-98, Mowiol 15-99 and Mowiol 28-99.

"Sol.-PVP": soluble polyvinylpyrrolidone derivatives. Preferred examples of soluble PVPs include Kollidon 12 PF, Kollidon 17 PF, Kollidon 25, Kollidon 30, Kollidon 30 LP and Kollidon 90 F.

"CL-PVP": insoluble crosslinked polyvinylpyrrolidone derivatives. Preferred examples of CL-PVPs include Kollidon CL, Kollidon CL-F, Kollidon CL-SF and Kollidon CL-M.

"VP/VAc": copolymers from 1-vinyl-2-pyrrolidone and vinyl acetate, preferably in a mass ratio of 6:4. Preferred examples of VP/VAc include Kollidon VA64 and Kollidon VA64 fine.

"SxS pressure-sensitive adhesive": styrene block copolymer-based adhesives, which have non-elastomeric styrene blocks at their ends and elastomeric blocks in the middle (see above).

"Polysaccharides": molecules in which at least the monosaccharide molecules are connected via a glycosidic bond. Preferred examples include alginates, agar-agar, carrageenan, guar gum, glucomannan, locust bean gum, oat beta glucan, pectin, xanthan, guar hydroxypropyl trimonium chloride and sodium hyaluronate.

"Mod. celluloses": modified celluloses. Preferred examples are ethyl cellulose (EC), MC (Metolose®, methyl cellulose, cellulose-methylated), HPMC (Metolose®, MHPC, hypromellose, hydroxypropyl methyl cellulose), HPMC-phthalate (HPMC-P, hypromellose phthalate), AQOAT (HPMC-AS, hypromellose-acetate-succinate), L-HPC (hydroxypropyl cellulose, low-substituted), carboxy methyl cellulose (CMC) and microcrystalline cellulose (MCC).

"Standard silicon adhesive": silicon polymer that includes the following three classes:

low-tack silicon adhesives (low-tack=identifier 440X), medium-tack silicon adhesives (medium-tack=identifier 450X), and high-tack silicon adhesives (high-tack=identifier 460X). Selected examples are BIO-PSA 7-4401, BIO-PSA 7-4402, BIO-PSA 7-4501, BIO-PSA 7-4502, BIO-PSA 7-4601 and BIO-PSA 7-4602.

"AC silicon adhesives": amine-compatible silicon adhesive that includes the following three classes:

low-tack silicon adhesives (low-tack=identifier 410X), medium-tack silicon adhesives (medium-tack=identifier 420X), and high-tack silicon adhesives (high-tack=identifier 430X). Selected examples are BIO-PSA 7-4101, BIO-PSA 7-4102, BIO-PSA 7-4201, BIO-PSA 7-4202, BIO-PSA 7-4301 and BIO-PSA 7-4302.

"HM silicon adhesives": so-called hot-melt silicon adhesives that are solvent-free and that become liquid under heat treatment.

"PIB": mixture of a PIB with a higher molecular weight, especially a Mw of 250,000 to 600,000 g/mol, and of a PIB with a lower molecular weight, especially a Mw of approximately 36,000 g/mol, and preferably a low-molecular-weight polybutylene.

"BIB": copolymers from butene and isobutylene such as, for instance, PAR950.

"Polybutene": thermoplastic polymer from butene-1. In contrast to polyisobutylene with a branched structure, in the case of PB, the monomers are linear and are arranged largely isotactically, whereby high molar masses of 700,000 to 3,000,000 g/mol are obtained in total. Indopol is mentioned here by way of an example.

"EVA": copolymers from ethylene and vinyl acetate.

| Middle layer | Inner layer |
| --- | --- |
| TH-PVA | standard silicon adhesives |
| VH-PVA | standard silicon adhesives |
| Sol. PVP | standard silicon adhesives |
| CL-PVP | standard silicon adhesives |
| Vp/VAc | standard silicon adhesives |
| Polysaccharides | standard silicon adhesives |
| Mod. celluloses | standard silicon adhesives |
| TH-PVA | AC silicon adhesives |
| VH-PVA | AC silicon adhesives |
| Sol. PVP | AC silicon adhesives |
| CL-PVP | AC silicon adhesives |
| Vp/VAc | AC silicon adhesives |
| Polysaccharides | AC silicon adhesives |
| Mod. celluloses | AC silicon adhesives |
| TH-PVA | SxS pressure-sensitive adhesives |
| VH-PVA | SxS pressure-sensitive adhesives |
| Sol. PVP | SxS pressure-sensitive adhesives |
| CL-PVP | SxS pressure-sensitive adhesives |
| Vp/VAc | SxS pressure-sensitive adhesives |
| Polysaccharides | SxS pressure-sensitive adhesives |
| Mod. celluloses | SxS pressure-sensitive adhesives |
| TH-PVA | PIB |
| VH-PVA | PIB |
| Sol. PVP | PIB |
| CL-PVP | PIB |
| Vp/VAc | PIB |
| Polysaccharides | PIB |
| Mod. celluloses | PIB |
| TH-PVA | polybutene |
| VH-PVA | polybutene |
| Sol. PVP | polybutene |
| CL-PVP | polybutene |
| Vp/VAc | polybutene |
| Polysaccharides | polybutene |
| Mod. celluloses | polybutene |
| TH-PVA | EVA |
| VH-PVA | EVA |
| Sol. PVP | EVA |
| CL-PVP | EVA |
| Vp/VAc | EVA |
| Polysaccharides | EVA |
| Mod. celluloses | EVA |
| TH-PVA | BIB |
| VH-PVA | BIB |
| Sol. PVP | BIB |
| CL-PVP | BIB |
| Vp/VAc | BIB |
| Polysaccharides | BIB |
| Mod. celluloses | BIB |

In an alternative embodiment, the inner layer is configured to be non-adhesive. For instance, a non-adhesive dressing is advantageous, especially in the case of open or exuding wounds.

In another preferred embodiment, the inner layer is configured in such a way that it aids wound healing in that, for example, it absorbs wound secretions or even forms a non-adhesive gel with the wound.

Such wound dressings are known to the person skilled in the art and they contain, for instance, hydrocolloid, hydrogel, alginate (preferably calcium-alginate) or polymer foam.

Examples of such hydrogel-like materials are described with reference to the following patent specifications:

CA-A 1 180 622: gelatins+polyethylene oxide+polyethylenimine

DE-C 28 49 570: hydrophilic poly(meth-)acrylic acid derivative in the presence of polysaccharide/protein DE-C 30 31 304 base: hydrophilic ethylenically unsaturated monomers, crosslinked with difunctional compounds EP-B 0 099 758: synthetic collagen or alginates and other biopolymers EP-B 0 262 405: polysodium acrylate/polyacrylic acid/acryloylamide and other acrylamide derivatives EP-B 0 272 074: copolymers from unsaturated monomers containing carboxyl groups+disaccharides or oligosaccharides U.S. Pat. No. 3,249,109: gelatin, water, polyvalent alcohols, pectin U.S. Pat. No. 4,243,656: polyacrylate dispersion+moisture absorber, gelatin, water WO 2010/046095 A1: polyurethane gel foam In a preferred embodiment, the hydrogel is made up of the following constituents (see DE 3903672 C1):

a) 20% to 70% by weight of at least one polyvalent alcohol
b) 10% to 35% by weight of at least one natural gelling agent (biopolymer)
c) 0.05% to 12% by weight of at least one non-crosslinked copolymer from one or more vinyl carboxylic acids and their salts (synthetic polymer)
d) 0.05% to 10% by weight of a crosslinking agent
e) 0% to 50% by weight of water or a physiological saline solution.

Here, the polyvalent alcohol is preferably glycerin that can be used either alone or in a mixture with additional polyvalent alcohols. Other polyvalent alcohols are ethylene glycol, diethylene glycol, 1,2-propanediol, 1,3-propanediol, 1,2-butanediol, 1,3-butanediol, 2,3-butanediol, 1,4-butanediol, glycerin monoacetate or a mixture of these alcohols. The natural gelling agent (biopolymer) used here is primarily gelatin, either alone or in a mixture with other biopolymers, preferably alginates. Special preference is given to a combination of gelatin and sodium alginate at the weight ratio of 5:1 to 30:1. Collagens and pectins are examples of additional biopolymers that are used either alone or in a mixture. The non-crosslinked copolymer used as the synthetic polymer is made up of at least one vinyl carboxylic acid and at least one of its alkali or ammonium salts. As vinyl carboxylic acids, preference is given to acrylic acid, methacrylic acid and/or β-acryloyloxypropionic acid. Other suitable vinyl carboxylic acids include vinylacetic acid, maleic acid, fumaric acid, crotonic acid, aconitic acid, itaconic acid and mixtures of these acids. The crosslinking agents used according to the invention are preferably selected from the group of metal chelates, orthotitanic acid esters, epoxides, aziridines, triazines or melamine-formaldehyde resins. In this context, special preference is given to the aziridines and the group of the metal chelates, for example, the acetyl acetonates, for instance, the transition-metal acetyl acetonates such as titanium or zirconium acetylacetonate. The crosslinking agent brings about the crosslinking of biopolymers with synthetic polymer to form predominantly three-dimensional networks.

In a preferred embodiment, the inner layer is a hydrocolloid. Concerning the term "hydrocolloid" as set forth within the scope of the present invention, it should be understood in a very broad sense. In general, hydrocolloids refer to at least partially water-soluble, natural or synthetic polymers that form gels or viscous solutions or suspensions in aqueous systems. These are normally substances that belong to the substance classes of proteins or polysaccharides, whereby numerous hydrocolloids come from nature, especially from land plants, algae, animals and bacteria. Hydrocolloids are often used as thickening agents in cosmetics and products in the food industry. For more detailed information about the term hydrocolloids, reference can especially be made to Römpp Chemielexikon [Römpp's Chemical Encyclopedia], $10^{th}$ edition, published by Georg Thieme Verlag, Stuttgart/New York, key word: "Hydrocolloids", page 1837, including the literature referred to there, whereby in this context, the appertaining content is hereby fully encompassed by reference.

Here, it is particularly advantageous for the hydrocolloid to be gelatin and/or collagen, and especially collagen.

Collagen comprises long-fibered, linear-colloidal and high-molecular scleroproteins of the extracellular matrix that occur in connective tissue, especially in the skin, in cartilage, and in tendons, ligaments and blood vessels as well as in the base substance of the bones of vertebrates containing protein, but also in phylogenetically early life forms such as sponges or sea anemones. The fibrous structure of collagen is especially brought about by the occurrence of glycine at every third position in the amino acid sequence, since glycine, as a very space-saving amino acid, brings about a special helical secondary structure in proteins. The amino acids tryptophan and tyrosine, also known as so-called helix breakers, as well as the amino acid cysteine, which forms disulfide bridges, in contrast, are generally not present in collagens. Furthermore, for more detailed information about the term collagen, reference can especially be made to Römpp Chemielexikon [Römpp's Chemical Encyclopedia], $10^{th}$ edition, published by Georg Thieme Verlag, Stuttgart/New York, key word: "Collagens", pages 796 and 797, as well as the literature referred to there, whereby in this context, the appertaining content is hereby fully encompassed by reference.

Especially as far as the use of collagen within the scope of the wound dressing according to the invention is concerned, this makes it possible to significantly improve the process of wound healing. In particular, collagen has a protease-inhibiting effect that serves to lower the elevated protease level in the wound region being is detrimental to wound healing. After all, if the protease level in the wound region is elevated, this often leads to an uncoordinated wound healing and to the destruction of growth factors, since the latter are degraded by proteases such as, for example, neutrophilic elastases or matrix-metallo-proteases (MMPs). Moreover, collagen stimulates the formation of vascular structures and connective tissue, thereby promoting the restoration of the structural stability of the tissue. In this context, the use of collagen as a hydrocolloid can promote wound healing in an extremely efficient manner.

Similar remarks also apply to gelatin, which can likewise be used as a hydrocolloid in a preferred manner in the wound dressing. Normally and within the scope of the present invention, the term "gelatin" refers to a polypeptide that is obtained under acidic or alkaline conditions primarily by means of hydrolysis of the collagen present in the skin and bones of animals. Here, obtaining gelatin under acidic conditions results in so-called type A gelatin, while doing so under alkaline conditions results in so-called type B gelatin. In water, especially under the simultaneous influence of heat, gelatin first swells up strongly and dissolves in it, forming a viscous solution that finally solidifies gelatinously below 35° C. [95° F.]. For more detailed information about the term gelatin, reference can especially be made to Römpp Chemielexikon [Römpp's Chemical Encyclopedia], $10^{th}$ edition, published by Georg Thieme Verlag, Stuttgart/New York, key word: "Gelatins", page 1484, including the literature referred to there, whereby in this context, the appertaining content is hereby fully encompassed by reference.

Furthermore, concerning the hydrocolloid layer, especially the collagen layer, it can be provided according to the invention that the layer containing hydrocolloid, preferably collagen, is based on a hydrocolloid non-woven and/or hydrocolloid foam, preferably collagen non-woven and/or collagen foam. In this context, it can be provided that the hydrocolloid layer is made on the basis of hydrocolloid non-woven and/or hydrocolloid foam, preferably collagen non-woven and/or collagen foam, of porcine, bovine and/or equine origin, especially preferably on the basis of hydrocolloid non-woven and/or hydrocolloid foam, preferably collagen non-woven and/or collagen foam of porcine origin.

In a manner especially preferred according to the invention, it can be provided that the layer containing the hydrocolloid, preferably collagen, is made up of a hydrocolloid non-woven and/or hydrocolloid foam, preferably collagen non-woven and/or a collagen foam, especially a hydrocolloid non-woven and/or hydrocolloid foam, preferably collagen non-woven and/or a collagen foam, of porcine, bovine and/or equine origin, preferably a hydrocolloid non-woven and/or hydrocolloid foam, preferably collagen non-woven and/or a collagen foam of porcine origin.

When compared to conventional materials for the production of wound dressings, it is the case that hydrocolloid non-woven or hydrocolloid foam, preferably collagen non-woven or collagen foam, is especially associated with the advantage that the material does not adhere to the wound bed or to the wound surface, and yet it provides a good adhesion to the surface. Moreover, it is particularly advantageous if wound dressings on the basis of hydrocolloid foam or hydrocolloid non-woven, especially collagen non-woven or collagen foam, do not shed fibers or any solid constituents or particles on the wound, thus preventing the penetration or an additional transfer of foreign matter.

In this context, it has proven to be especially advantageous if the wound dressing contains hydrocolloid foam, especially collagen foam, that is to say, a hydrocolloid or collagen that has been solidified or expanded to form a foam, especially since, through the pores that are present in the hydrocolloid foam or collagen foam, large amounts of wound secretions can efficiently flow away from the wound region, thereby preventing moisture from accumulating and also preventing substances that are present in the wound secretion and that are detrimental to wound healing from being in contact with the wound itself for too long. And yet, the chemical and physical properties of solidified and expanded hydrocolloid or collagen (in other words hydrocolloid foam or collagen foam) prevent the wound from drying out.

Furthermore, such foams can be very well adapted to the shape of the wound bed, that is to say, they can cover the wound over the entire surface area, without bulges or the like being formed. Moreover, the use of a hydrocolloid foam or collagen foam translates into a very good gas permeability. This is especially associated with the advantage that the wound is very thoroughly gassed with the NO that is generated in the wound dressing, which, on the one hand, promotes the physiological wound healing process and, on the other hand, also prevents the growth of germs.

As a result, thanks to the provision of the colloid layer or collagen layer, on the one hand, wound secretions are efficiently carried away and, on the other hand, good NO gas permeability is assured.

Moreover, as far as the hydrocolloid layer, especially the collagen layer, is concerned, according to the invention, it can be provided that such a layer can be obtained by applying a dispersion or solution of a hydrocolloid foam, preferably a collagen, onto a carrier and subsequently drying it, especially by lyophilization (freeze-drying), preferably while concurrently expanding the hydrocolloid foam, preferably the collagen. A hydrocolloid suspension or solution, preferably a collagen suspension or solution that is suitable according to the invention, can especially be obtained by suspending or solubilizing the hydrocolloid, especially the collagen, in water, especially in extra-pure water or in disinfected or degermed or sterilized water. Here, the hydrocolloid, especially collagen, can preferably be present in the suspension or solution in a quantity ranging from 0.1% to 5% by weight, especially 0.5% to 4% by weight, preferably 0.7% to 3% by weight, especially preferably 1% to 2% by weight, relative to the hydrocolloid suspension or hydrocolloid solution, preferably collagen suspension or collagen solution. The dried and expanded hydrocolloid, preferably collagen, can finally be removed from the carrier and then used for the production of the wound dressing. In order to ensure the desired properties, the hydrocolloid or the appertaining layer with the hydrocolloid can have a defined residual moisture, which is known to the person skilled in the art.

The hydrocolloid, preferably the collagen, the hydrocolloid layer, especially the collagen layer, can especially be of porcine, bovine and/or equine origin, especially porcine skin.

When it comes to the dimensions of the layer containing at least one hydrocolloid, preferably collagen, said layer preferably has a thickness in the range from 0.01 mm to 100 mm, especially 0.02 mm to 50 mm, preferably 0.05 mm to 10 mm. Depending on the severity of the wound that is to be treated and depending on the amount of wound exudation, it is advantageous for the layer containing a hydrocolloid, preferably collagen, to be particularly thick, especially in case of a great deal of secretion of lymph (especially, for example, during the exudative phase of wound healing). In contrast, in the case of wounds that are already well advanced in the healing process, it is usually sufficient to use much thinner hydrocolloid or collagen layers. Thus, according to the invention, it is possible to adapt the thickness of the hydrocolloid or collagen layer to the specific requirements.

Advantageous combinations of polymers of the middle layer and of the inner layer that promotes wound healing are listed in the table below.

| Middle layer | Inner layer |
| --- | --- |
| TH-PVA | polyurethane (gel) foam |
| VH-PVA | polyurethane (gel) foam |
| Sol. PVP | polyurethane (gel) foam |
| CL-PVP | polyurethane (gel) foam |
| Vp/VAc | polyurethane (gel) foam |
| Polysaccharides | polyurethane (gel) foam |
| Mod. celluloses | polyurethane (gel) foam |
| TH-PVA | matrix with Ca alginate |
| VH-PVA | matrix with Ca alginate |
| Sol. PVP | matrix with Ca alginate |
| CL-PVP | matrix with Ca alginate |
| Vp/VAc | matrix with Ca alginate |
| Polysaccharides | matrix with Ca alginate |
| Mod. celluloses | matrix with Ca alginate |
| TH-PVA | hydrogel (foam) |
| VH-PVA | hydrogel (foam) |

-continued

| Middle layer | Inner layer |
| --- | --- |
| Sol. PVP | hydrogel (foam) |
| CL-PVP | hydrogel (foam) |
| Vp/VAc | hydrogel (foam) |
| Polysaccharides | hydrogel (foam) |
| Mod. celluloses | hydrogel (foam) |
| TH-PVA | hydrocolloid (foam) |
| VH-PVA | hydrocolloid (foam) |
| Sol. PVP | hydrocolloid (foam) |
| CL-PVP | hydrocolloid (foam) |
| Vp/VAc | hydrocolloid (foam) |
| Polysaccharides | hydrocolloid (foam) |
| Mod. celluloses | hydrocolloid (foam) |
| TH-PVA | Suprasorb ® |
| VH-PVA | Suprasorb ® |
| Sol. PVP | Suprasorb ® |
| CL-PVP | Suprasorb ® |
| Vp/VAc | Suprasorb ® |
| Polysaccharides | Suprasorb ® |
| Mod. celluloses | Suprasorb ® |
| TH-PVA | collagen (foam) |
| VH-PVA | collagen (foam) |
| Sol. PVP | collagen (foam) |
| CL-PVP | collagen (foam) |
| Vp/VAc | collagen (foam) |
| Polysaccharides | collagen (foam) |
| Mod. celluloses | collagen (foam) |
| TH-PVA | gelatin (foam) |
| VH-PVA | gelatin (foam) |
| Sol. PVP | gelatin (foam) |
| CL-PVP | gelatin (foam) |
| Vp/VAc | gelatin (foam) |
| Polysaccharides | gelatin (foam) |
| Mod. celluloses | gelatin (foam) |

The outer layer provided in some embodiments preferably comprises at least one hydrophobic polymer. The at least one hydrophobic polymer can preferably be a polyisobutylene (PIB) or a mixture of various polyisobutylenes (PIBs), polybutylene, butyl rubber, a styrene-copolymer, a styrene-butadiene-styrene block copolymer, a styrene-isoprene copolymer, styrene isoprene, a silicon polymer or a mixture of various silicon polymers or a mixture or a copolymer thereof.

Special preference is given to a PIB, a mixture of various PIBs, a silicon polymer, as well as a mixture of various silicon polymers. Very special preference is given to a PIB as well as to a mixture of various PIBs.

For the rest, regarding the outer layer, reference is hereby made to the information pertaining to the inner layer. As already mentioned, the outer and inner layer can have different polymer compositions. Preferably, however, the outer layer has the same polymer composition as the inner layer.

The multilayered NO module of the present invention optionally has a backing layer that is inert vis-à-vis the components of the matrix. The backing layer is preferably a film that is impermeable for the active ingredients. Such a film can consist of polyethylene terephthalate (PET), polyester, polyamide, polyethylene, polypropylene, polyurethane, polyvinyl chloride or a combination of the above-mentioned materials. If so desired, these films can be coated with an aluminum foil or an aluminum vapor deposit. The thickness of the backing layer can be between 10 μm and 100 μm, preferably between 15 μm and 40 μm.

The backing layer, at least in a partial area, is advantageously permeable to the electromagnetic radiation that is intended to photolytically cleave the nitric oxide donors in the NO module.

The multi-layered NO module of the present invention can optionally comprise a protective layer or protective film that is removed immediately before the NO module is used, especially immediately before it is brought into contact with the skin. The protective layer or protective sheet can preferably be made of polyester, polyethylene terephthalate (PET), polyethylene or polypropylene that can optionally be coated with aluminum foil or an aluminum vapor deposit or else fluoropolymers. Typically, the thickness of a protective layer or protective sheet can be in the range between 50 μm and 150 μm. In order for the protective layer or protective sheet to be removed when the medical dressing is going to be used, the protective layer or protective sheet can contain separate protective layers or protective sheets that have overlapping ends, similar to the type used in most conventional adhesive bandages.

In an especially preferred embodiment, the multi-layered NO module according to the invention consists of precisely two layers: a middle layer containing the nitric oxide donors and an inner layer, whereby the inner layer is directly adjacent to the layer containing nitric oxide donors. This NO module also comprises a backing layer and a protective layer.

In a likewise preferred embodiment, the multi-layered NO module according to the invention consists of precisely three layers: a middle layer containing nitric oxide donors, an inner layer and an outer layer, whereby the inner layer and the outer layer are directly adjacent to the layer containing nitric oxide donors. This medical dressing also comprises a backing layer and a protective layer.

In another embodiment of the invention, the medical dressing is configured in such a way that the release of NO into the environment is reduced or completely prevented.

In another embodiment, the NO module is coupled to an NO sensor, so that, as feedback to the measured NO value, the magnitude of the NO generation can be flexibly adapted.

This NO sensor, as a measuring device for quantifying the NO, can be situated in one of the layers of the NO module, that is to say, for example, in the backing layer, in the protective layer, in the middle layer or in the inner layer. Moreover, it can be situated between the inner layer and the skin or else on the outside (that is to say, above the backing layer or the protective layer) of the medical dressing. In a special embodiment, the NO sensor-associated control ensures that the NO-generating unit completely stops generating NO if a critical NO value is exceeded.

In one embodiment of the invention, the NO module is actuated in such a way that the content of released NO is kept constant over the period of time of the treatment.

In an alternative embodiment of the invention, the NO module is actuated in such a way that the content of released NO increases or decreases over the period of time of the treatment.

In one embodiment of the invention, the NO module is configured as an easily replaced disposable article.

In another preferred embodiment, the NO module is configured in such a way that its shape permits error-free use in the medical dressing. Thus, it is preferably configured as an adhesive bandage or transdermal therapeutic system (TTS) that can only be attached to the radiation-emitting module in one orientation. This can be achieved, for example, by using Velcro to join the radiation-emitting module to the NO module. Moreover, the NO module or the radiation-emitting module can be provided with a locking mechanism that only permits the generation and/or release of the electromagnetic radiation by the radiation-emitting module if the NO module has been joined correctly, i.e. with a precise fit. Advantageously, the medical dressing can be provided here with a sensor that detects the correct orientation or locking of the radiation-emitting module and of the NO module, and this is then displayed to the user.

In this context, the source of electromagnetic radiation can be a glow-discharge lamp or a gas discharge lamp (low-pressure-discharging or high-pressure-discharging) coated with appropriate fluorochromes, light-emitting diodes (LED), organic light-emitting diodes (OLED), lasers or any other electromagnetic source of radiation that is capable of generating NO from the appertaining chemical precursors or substrates.

For an optimal cleavage of the photolabile NO donors that are dissolved or suspended in the NO module, the light source of the radiation-emitting module can emit electromagnetic radiation at wavelengths of 100 nm to 2000 nm or electromagnetic radiation of any other wavelength which, either alone or with the assistance of chemical, physical or biological methods, can induce a cleavage of nitric oxide donors and thus a release of nitric oxide.

In a preferred manner, the radiation-emitting module is connected to the NO module in such a way that they are both at defined distance that remains constant over their surface. This can preferably be achieved by means of a flexibly configured radiation-emitting module that can be placed onto the NO module.

In an alternative embodiment, in the case of a flat source of radiation (e.g. an LED panel), the radiation-emitting module is provided with a spacer that can thus establish a defined distance to the NO module.

In order to reduce, avoid or prevent possible contamination of the ambient air with NO or its oxidative reaction products, the medical dressing can have an exhaust system that draws off the harmful gases such as NO or $NO_2$ that might escape and then passes them through an activated carbon filter or through some other device that is capable of neutralizing or eliminating such reactive gas species.

In order to ensure safe use of the device according to the invention, the device has an electronically controlled, application-specific program selection, including a safety switch-OFF for the medical dressing, as well as appropriate sensors for NO, $NO_2$, temperature and safety as well as a remote control and the capability to be connected to external control and documentation units or applications. The safety management measures also include the electronically controlled application-specific and user-specific monitoring of the NO modules that are specifically filled, whereby they are preferably configured as replaceable disposable articles.

The multi-layered NO module according to the present invention can be obtained in that
(i) a solution containing nitric oxide donors and at least one hygroscopic polymer or copolymer is spread over the surface and dried, and
(ii) the layer thus obtained is laminated with another layer as well as with a layer that becomes permeable to NO during the treatment.

Preferably, the solution in step (i) contains at least one hydrophilic solvent, preferably ethanol and/or water.

Within the scope of the production of the multi-layered NO module according to the invention, all of the layers can be made by means of the classic techniques of dissolving, mixing, coating and temperature-regulated drying or else by shaping only by means of heat.

For this purpose, methods that have long since been familiar to the person skilled in the art can be used so that, first of all, individual layers can be applied onto prepared, dehesively finished support films which, as a rule, are made of polyethylene terephthalate (PET), by means of solvent-based coating methods using doctor blades, slot dies, spray nozzles or rollers to apply uniform layer thicknesses that preferably have an application weight of 15 $g/m^2$ to 40 $g/m^2$ after drying so as to form the inner layer and, if applicable, 5 $g/m^2$ to 40 $g/m^2$ so as to form the outer layer as well as, at the maximum, an application weight of 40 $g/m^2$ after drying so as to form the middle layer containing nitric oxide donors. In the case of graduated silicon polymerization on both sides, the layer can be wound up directly with the substrate itself. Subsequently, the active ingredient is absorbed in a non-tacky polymer auxiliary, and a uniform inner phase is formed out of the water-absorbing or water-swelling polymer through the modality of coating onto prepared, dehesively finished support films by means of solvent-based coating methods using doctor blades, slot dies, spray nozzles or rollers to apply uniform layer thicknesses having the above-mentioned values for the application weight after drying.

The person skilled in the art can produce these thin layers nowadays by employing conventional coating, drying and extrusion methods. The nitric oxide donors can be added in one or more layers—middle layer or separating layers—so as to contain solvents when intermediate drying processes have been carried out and so as to be free of solvents when the nitric oxide donors are liquid at the processing temperature or else when another solvent that remains in the formulation is added. In any case, due to the short diffusion paths, a distribution of the active ingredient in the system components, if desired, is easily possible within hours to days after the production.

The layers can be produced in any desired sequence and laminated onto each other using processes that are familiar to the person skilled in the art. An essentially NO-impermeable backing layer can be provided that does not stay behind on the system during the application and that protects the NO module from sticking to textiles. Moreover, a removable protective layer can be provided that is removed before the NO module is applied onto the skin.

In a preferred embodiment, the multi-layered NO module according to the invention is produced by means of the methods described in German patent applications DE 101 47 036 A1 and DE 10 2008 038 595 A1. The methods described there are especially advantageous for coating a substrate that is coated with a protective film, as a result of which a particularly uniform adhesive application is achieved.

In alternative embodiments, however, the following application and lamination systems can be used for the production of the NO module according to the invention:
knife system; double side system; comma bar system; case knife system; engraved roller system; 2-roller system; 3-roller system; micro-roller system; 5-roller system; reverse roll system; rotary screen system; dipping system; slot die system; curtain coating system; hot-melt slot die system; powder scattering system.

In a preferred embodiment, the NO module according to the invention is produced by means of the so-called slot die system, which is based on a die technology. Here, the die is a closed application system that consists of a die chamber into which the coating raw material that is to be applied is pumped. The geometry of the die, which is determined specifically for each coating raw material in terms of its flow pattern, guarantees a uniform outflow of the coating raw material from the outlet slot. A (micro)pump conveys the coating medium to the die with a high degree of metering precision. The coating quantity can be precisely defined on the basis of the pump speed. Moreover, the outflow slot as well as the product speed define the application weight. Thus, very thin layers of less than 5 μm are possible as a function of the raw material viscosity.

In one embodiment of the invention, the NO is generated by a plasma-chemical modality. Aside from the use of "technical" NO gases for medical applications, there are methods for the plasma-chemical production of nitric oxide. International patent application WO 95/07610 A, U.S. Pat. No. 5,396,882 A and German patent application DE 198 23 748 A are publications that disclose methods for the plasma-chemical production of NO in which NO is produced under the effect of a glow discharge, spark discharge or arc discharge in a processing gas containing nitrogen ($N_2$) and oxygen ($O_2$). When a gas discharge of the described type is carried out at excessively low temperatures (as is observed in case of a glow discharge), it results in a low efficiency of the NO production in a gas mixture. Moreover, primarily the $NO_2$ radical ($NO_2$.), which is undesired for inhalation purposes, is generated under these conditions. In order to remove the $NO_2$ radical from the inhalation gas, it is necessary to employ complex absorber technology. The drawback of an absorber is especially the fact that the absorber material has to be frequently replaced or regenerated. A spark discharge or an arc discharge, both of which have higher energy than a glow discharge, brings about a relatively pronounced heating of the gas, resulting in a commensurately efficient production of NO. The high thermal load exerted on the electrodes, especially at the point of contact of the spark, however, disadvantageously causes severe electrode erosion, that is to say, progressive disintegration of the electrode material. Due to this electrode erosion, the method is, on the one hand, maintenance-intensive because the electrodes are highly prone to wear. On the other hand, it has to be prevented that patients are exposed to the eroded electrode material that has been finely dispersed in the gas. This necessitates a laborious purification of the gas.

Within the scope of the present invention, NO is produced by means of photolysis of a photolabile substance. According to this method, for instance, the nitrite ions ($NO_2^-$) present in a solution containing nitrite (e.g. sodium nitrite) are cleaved (photolysis) by means of electromagnetic radiation (e.g. UVA radiation at wavelengths between 320 nm and 440 nm), as a result of which NO is generated. Under reductive conditions or in an inert gas atmosphere (e.g. nitrogen), the decomposition of nitrite induced by the electromagnetic radiation takes place via different channels, some of which are also parallel but weighted differently thermodynamically. It can be assumed that in channel 1 (Reactions 1 to 5), UVA radiation (with an optimum at 354 nm to 366 nm) cleaves nitrite to form the nitric oxide radical (NO.) and the oxygen radical anion (O.$^-$) (Equation 1). The latter product subsequently initiates the formation of the reactive hydroxyl radical (OH.) (Equation 2) in aqueous solutions. The hydroxyl radical reacts with nitrite, leading to the formation of the nitrogen dioxide radical ($NO_2$.) (Equation 3). This can then further react with nitric oxide to form dinitrogen trioxide ($N_2O_3$) (Equation 4).

  (1)

  (2)

  (3)

  (4)

  (5)

It seems that, in channel 2 (Equations 6 to 10), hydroxyl radicals do not play any role under the conditions cited, although a "hydrated" electron ($e^-_{hyd}$) as well as a nitrogen dioxide radical are formed (Equation 6). In the presence of an excess of nitrite, the electron is transferred to the nitrite, and the resultant nitrite anion (Equation 7) is reduced in water to form the NO radical (Equation 8). The following reactions in Equations (9) and (10) correspond to those in Equations (4) and (5). In this process, the weighting of channel 1 to channel 2 forms a ratio of about 40:60.

  (6)

  (7)

  (8)

  (9)

  (10)

As can be seen from Reactions 1 to 10, the photolytic decomposition of nitrite is accompanied by a parallel production of reactive and cytotoxic chemical species. Moreover, from the reactions in Equations (4) and (9), it can also be seen that $NO_2$ radicals ($NO_2$.) can undergo a backward reaction with the NO formed in Equation (1).

It has been recognized (European patent application EP 1903003 A1) that, through the use of at least one system that breaks down or neutralizes $NO_2$ radicals or oxygen species during the generation of nitric oxide, the formation of the above-mentioned reactive intermediate products of light-induced nitrite decomposition ($NO_2$., O.$^-$, OH., $e^-_{hyd}$) is suppressed or else they are eliminated, while, at the same time, there is no reduction in the generation of nitric oxide. Therefore, the yield of freely available NO and the purity of the gas are enhanced.

The increase in the release of NO as well as the high degree of purity stem from a reaction-induced elimination of the reactive intermediate products, for instance, according to the following Reactions (11) to (17).

  (11)

  (12)

  (13)

  (14)

  (15)

  (16)

  (17)

(Abbreviations: RS$^-$=thiol; RSNO=S-nitrosothiol; RS.=thioyl radical; BA=benzoic acid; VitC=vitamin C, ascorbate, ascorbic acid; VitC.=the radical of VitC; Trol=trolox; Trol.=the radical of trolox)

Thanks to the presence of these or other functionally equivalent systems during the formation of nitric oxide, this method (European patent application EP 1903003 A1) accounts for a high yield of nitric oxide while, at the same time, the formation of undesired (poly)oxidized nitrogen oxides, especially $NO_2$. as well as of hydroxyl radicals and reactive hydrated electrons is effectively prevented, or else these substances are eliminated after having been formed, or else they can only be produced in such small quantities that they remain in solution and cannot change over to the gas phase. Therefore, these substances cannot cause, for example, any pathologically relevant damage due to inhalation of the inhalation gases.

Substances (antioxidants) that break down or neutralize reactive nitrogen species (ROS) or nitrogen oxide species (RNS) are preferably used as the systems that break down or neutralize reactive nitrogen oxide species (e.g. nitrogen dioxide radicals) or reactive oxygen species. It is likewise preferred for these to be ascorbic acid, ascorbate, vitamin E and its derivatives, thiols, other antioxidants, radical traps or enzymes that break down ROS and RNS.

Moreover, it has been found that the binding or elimination of the above-mentioned reactive intermediate products of light-induced nitrite decomposition ($NO_2.$, $O.^-$, $OH.$, $e^-_{hyd}$) can also take place in the neutral pH range, whereby a maximum NO release with a maximum level of purity can be obtained from nitrite.

Acidic conditions (pH<7.0) are conducive to "spontaneous" nitrite decomposition in aqueous solutions. In accordance with Equations 18 to 20, the nitrite anion ($NO_2^-$) in aqueous solutions is in a state of equilibrium with its conjugated acid, namely, nitrous acid ($HNO_2$). $HNO_2$, in turn, is in a state of equilibrium with dinitrogen trioxide ($N_2O_3$), which spontaneously decomposes to form NO. and $NO_2$.

$$NO_2^- + H^+ \leftrightarrows HNO_2 \tag{18}$$

$$2HNO_2 \leftrightarrows N_2O_3 + H_2O \tag{19}$$

$$N_2O_3 \leftrightarrows NO. + NO_2. \tag{20}$$

Therefore, in one embodiment of a described method (European patent application EP 1903003 A1), the UVA-induced generation of nitric oxide preferably takes place within a pH range from 0 to 12, particularly from 1 to 10, particularly preferred from 1.5 to 6, especially from 2 to 6 and very especially from 2.5 to 4.

Depending on the nitrite or antioxidant concentration employed as well as on the magnitude of the physical decompensation stimulus used that leads to the decomposition of the nitrite, a high concentration of nitric oxide can be obtained by means of the cited method (European patent application EP 1903003 A1).

In a solution, the quantity of generated nitric oxide can be controlled by means of the employed concentration of the agents that release nitric oxide and by means of the physical and/or chemical induction that is responsible for the release of nitric oxide from the agents.

In this context, the expression "physical and/or chemical induction" refers not only to the intensity of the electromagnetic radiation but also to the duration of the exposure to which the reaction solution is subjected; it also generally refers to the reaction parameters that have an influence on the formation of nitric oxide itself as well as on the concentration of nitric oxide. Generally speaking, these parameters include the pH value of the reaction solution, the redox status of the reaction solution, the temperature of the reaction solution, the surface area exposed to radiation, the duration of action of an induction quantity on the agents that release nitric oxide, the distance between the source of electromagnetic radiation and the reaction solution, the spectrum of the source of electromagnetic radiation, the absorption, transmission and reflection properties of the reaction solution, the concentration of biological or chemical catalysts or mediators which, even outside of the "typical" physical-chemical conditions needed for an optimal NO release, nevertheless allow NO to be released from NO-generating substances through catalysis or through appropriate acceptor properties. In particular, this expression refers to chromophores and other substances by means of which, for example, electromagnetic radiation outside of the UVA spectrum could also be capable of allowing NO to be released from the appropriate NO-forming agents.

Thus, for instance, at induction quantities that are kept constant, the use of varying concentrations of the substance(s) that release nitric oxide makes it possible to release varying amounts of nitric oxide.

Moreover, at a constant concentration of the substance(s) that release nitric oxide, the release of nitric oxide can be changed by varying the setting parameters of the appertaining induction quantities. Therefore, at an induction quantity that is kept constant, the use of high concentrations of the NO-releasing substances makes it possible to release large amounts of NO and vice versa. At a constant concentration of the NO-releasing substance, the generation of NO can be changed by varying the setting parameters of the appertaining induction quantities. In this context, the setting parameters can be employed alternatively to or simultaneously for the regulation of the NO generation. Particularly by means of the simultaneous regulation of the NO generation on the basis of several setting parameters, the method can be advantageously optimized in terms of the NO generation as well as in terms of the generation of undesired byproducts.

The substance that is employed for the release of nitric oxide as well as in the method according to the invention is fundamentally not subject to any restrictions, provided that it can release nitric oxide under the effect of electromagnetic radiation. For instance, it can be selected from among the group consisting of:

(a) pure substances or substance mixtures that generate nitric oxide under the effect of electromagnetic radiation;

(b) substance mixtures which, in addition to the substances or substance mixtures cited in (a), also contain auxiliary substances that are selected from the group consisting of photoacceptors, photoamplifiers, transition metals, particularly copper ions, for purposes of generating nitric oxide either spontaneously or under physical or chemical influences; and (c) substances or substance mixtures which, only after a preceding chemical reaction employing the substances cited in (a) and, if applicable, the auxiliary substances cited in (b), generate nitric oxide either spontaneously or under physical or chemical influences when exposed to electromagnetic radiation.

Moreover, the substances described in (a) can additionally release nitric oxide due to temperature changes and/or changes in moisture and/or changes in the pH of their solutions and/or changes in the redox status of their solutions.

The NO can be released from aqueous nitrite or S-nitrosothiol solutions. In this context, for practical reasons, preference is given to the use of an aqueous solution of sodium nitrite or S-nitrosothiols as the source of NO. The aqueous solution can have a concentration of NO donors preferably amounting to 0.001 mM to 10,000 mM, especially 0.2 mM to 6000 mM, particularly preferably 0.3 mM to 5000 mM, especially 0.4 mM to 2000 mM, very specially 0.5 mM to 1500 mM.

The technique for the radiation applied to the NO-generating initial substrates is familiar to the person skilled in the art in this field. Any electromagnetic radiation can be employed that is capable of breaking down photolabile NO derivatives while forming nitric oxide. For example, within the scope of the present invention, nitric oxide can be produced by means of photolytic cleavage using UVA radiation at wavelengths of, for example, 320 nm to 440 nm. However, it is likewise possible to employ electromagnetic radiation of any other wavelength which, either on its own or in conjunction with chemical, physical or biological methods, induces a direct photolytic cleavage of NO-generating donors (NO derivatives) or a photolytic cleavage induced or facilitated or catalyzed by other auxiliary substances.

The production of nitric oxide can also take place in solutions that are saturated with inert gases. In such solutions saturated with inert gases (nitrogen ($N_2$), helium ($H_2$), argon, etc.), the NO that is dissolved therein has a considerably longer useful life and can also remain in solution at higher concentrations. It is generally assumed that the maximum solubility of NO in aqueous solutions is approximately 2 mM. In this context, culture media or infusion media or infusion buffers, serum, blood, gels and all other substances that are capable of picking up gases can also be considered as aqueous solutions.

The nitric oxide produced by means of the photolysis of photolabile NO donors can be used, for instance, for inhalation purposes. Other specific areas of application are the stimulation of the metabolism of tissues through external application, the structural modification of organic as well as inorganic surfaces, sterilization or the creation of cytotoxicity. The nitric oxide generated by means of photolysis can also be used to apply gas to wounds, especially in order to heal chronic, non-healing, possibly bacteria-infested wounds. If the nitric oxide has been generated in saturated liquids, it can also be employed systemically for the treatment of hypertension. Finally, the nitric oxide can also be generated in carriers which are nitrosated with nitric oxide and which spontaneously release NO once again. The nitric oxide can also be employed for the production of a wide array of substances that bind NO (e.g. NO donors).

The quality of a gas that has been stored in or introduced into solutions and that is intended for medical applications has to meet stringent requirements. Even a slight contamination of the gas leads to the formation of undesired and conceivably toxic byproducts. The formation of these byproducts during prolonged storage of gas cylinders containing nitric oxide as well as during the production of nitric oxide using a plasma technique and also the removal of these radicals constitute a major technical as well as financial drawback. The advantages of the photolytic method for the production of solutions containing nitric oxide are the simplicity of the methods for the production of the gas containing NO, the particularly high degree of purity of the NO gas mixture produced, the low follow-up costs and the absence of storage costs, the very simple handling of the NO production as well as the purity control, and the incomparably favorable ratio of the production costs to the amount of NO gas produced.

Device According to the Invention

The present device according to the invention is a dressing that has a modular structure consisting of at least two layers and that is able to cleave incorporated photolabile nitric oxide donors in a closely adjoining absorption module by means of the emission of electromagnetic radiation from a light module, so that nitric oxide can be generated photolytically which can then be used to enhance medical therapies in humans and animals as well as to generate NO.

The advantages of such a device are quite evident. Due to the limited dissolving behavior of NO, it is possible to generate NO concentrations in the absorption module that are physiologically relevant but that are far below those that could be harmful to the health of humans. Moreover, a direct contact of the surface of the human body with the photolytically generated module of the device that releases nitric oxide translates into a considerably more accurate NO treatment than, for instance, with gas mixtures containing NO or with spontaneously disintegrating NO donors. Moreover, the fact that, depending on the level of the load with the appertaining NO donor, the device can be used by different end consumers—ranging from laypersons all the way to professionals—constitutes an essential advantage of the device according to the invention in comparison to other NO-based therapies.

The device according to the invention consists at least of a module that emits electromagnetic radiation (referred to within the scope of the invention as a radiation-emitting module) as well as of a closely adjoining module that contains the photolabile nitric oxide donors (referred to within the scope of the invention as an NO module).

The radiation-emitting module generates nitric oxide in the NO module by means of the photolytic cleavage of the photolabile or redox-labile nitric oxide donors that are incorporated therein. The NO module is an integral component of the entire device and it is permanently joined to the radiation-emitting module. As an alternative, the radiation-emitting module and the NO module can also be used separately from each other, namely, in that the radiation of the NO module is not applied in directly established contact with the radiation-emitting module, but rather at a certain distance therefrom.

It is important for the flooding of light through the NO module, together with the incorporated reaction substances that release nitric oxide, to be optimal or at a maximum with an eye towards an induced breakdown of the substance or a release of nitric oxide. For purposes of attaining optimal cleavage of the photolabile NO donors that are incorporated in the NO module, the radiation-emitting module can emit electromagnetic radiation at wavelengths of 100 nm to 2000 nm or else electromagnetic radiation of any other wavelength that, either on its own or in conjunction with chemical, physical or biological methods, can induce the cleavage of nitric oxide donors and thus the release of nitric oxide. In this context, the source of electromagnetic radiation can be a glow-discharge lamp or a gas discharge lamp (low-pressure-discharging or high-pressure-discharging) coated with appropriate fluorochromes, light-emitting diodes (LED), organic light-emitting diodes (OLED), lasers or any other electromagnetic source of radiation that is capable of generating NO from the appertaining chemical precursors or substrates.

Along with the electronic control unit for the light source, the source of electromagnetic radiation of the radiation-emitting module—which induces the NO release in the NO module in direct contact or else from a slight distance—can be installed in a part or in a housing in a compact manner, or else it can be physically separated from this control unit and only connected via a wired connection, or else it can even be completely separated, whereby in this case, the light source can be controlled remotely by the control unit.

The NO module should be made of a material or substance or carrier or medium that does not influence the properties of the energy of a source of electromagnetic radiation that is needed for an optimal release of nitric oxide or else which, owing to its properties, first creates or optimizes the light properties needed for a light-induced release of nitric oxide. Whereas the radiation-emitting module can be seen as a constant part of the device that is not consumed, the NO module can be considered to be an easily replaced or exchanged disposable article of the device. Here, the NO module can be viewed as a carrier medium that preferably contains chemically stable or stabilized, potentially NO-storing and thus potentially NO-releasing substances (for instance, organic or inorganic nitrates, nitrites, sulfur-nitroso, nitrogen-nitroso or oxygen-nitroso compounds, NO-metal compounds and NO-chelating substances), either on their own or in various combinations, which, in pure form or dissolved in various solvents, can release NO from the NO module in a reaction catalyzed, for example, by ions of transition metals, or else in a non-catalyzed reaction that is chemical and/or physically initiated.

The material or medium of the NO module containing the substances that potentially release NO once again can be a more or less viscous or thin or thick solution or liquid, a gel, a sheet, a film, a foam, a textile, a nonwoven, a plastic, a natural material or a carrier medium of any other class of substances that is capable or that can be made capable of storing or carrying NO-releasing substances or their stable donors, and capable of generating or releasing NO.

The advantage of using a replaceable or exchangeable NO module is that, by filling an NO module with reactive agents in different combinations and concentrations, different characteristic as well as application-specific and treatment-specific NO release patterns can be generated in or from the NO module. This makes it possible to achieve that the NO release patterns generated by the device allow optimization of the application so as to adapt it to the technical competence and level of responsibility of the end user, which is done through the selection of a specifically equipped NO module. Regarding the filling of the NO module, the amounts of the individual or combined NO donors (e.g. nitrite or S-nitrosothiols) selected are preferably 0.001 mM to 10,000 mM, particularly 0.01 mM to 6000 mM, particularly preferred 0.1 mM to 5000 mM, especially 0.4 mM to 2000 mM, very especially 0.5 mM to 1500 mM.

The NO generation in or from the NO module of the device according to the invention is preferably regulated on the radiation-emitting module or on the NO module through the manipulation of various setting parameters. Such setting parameters include the concentration of NO-releasing agents employed, the strength of the electromagnetic radiation and the properties of the additional physical and/or chemical induction quantities that are responsible for the release of NO from the agents. Moreover, the following parameters can be varied and employed, either individually or in different combinations, as possible induction quantities of an NO release from potentially NO-generating substances:
  the pH value,
  the redox status (the presence of reducing or oxidizing substances).
  the temperature,
  the current flow and/or the voltage;
  the surrounding pressure,
  the intensity of the electromagnetic radiation and the duration of the exposure to which the NO donor is subjected in the NO module,
  the surface exposed to the radiation,
  the duration of action of an induction quantity on the NO-releasing agents,
  the distance between the source of electromagnetic radiation and the reaction solution,
  the spectrum of the source of electromagnetic radiation,
  the absorption, transmission and reflection properties of the NO module layers,
  or the concentration of biological or chemical catalysts or mediators which, even outside of the "typical" physical-chemical conditions needed for an optimal NO release, allow NO to be released from NO-generating substances through catalysis or through appropriate acceptor properties (for instance, by means of chromophores and other substances with which, for example, even electromagnetic radiation that is outside of the UVA spectrum could be capable of enabling the release of NO from the appertaining NO-forming agents).

Regarding the latter point, it should be pointed out that, especially in the presence of ions of transition metals such as, for example, Cu', nitrite solutions can absorb light at considerably longer wavelengths than pure nitrite solutions can, and therefore the nitrite ion could also be cleaved by light at the wavelengths of 400 nm to 450 nm, thereby releasing NO.

Regarding the above-mentioned manipulated quantities for the device according to the invention, in case of an induction quantity that is kept constant, varying amounts of nitric oxide could be produced by using varying concentrations of the substances that release nitric oxide. On the other hand, in the case of a constant concentration of the substance that releases nitric oxide, the release of nitric oxide in the carrier medium can be changed by varying the setting parameters of the appertaining induction quantity.

The device according to the invention has a reliable safety-relevant and treatment-relevant sensor system (for example, for NO, $NO_2$, temperature, light intensity, skin reddening, time switch-OFF, etc.) as well as joining and connection possibilities to external equipment such as computers, smart phones, etc.). Moreover, all of the functions of the device can be directly controlled remotely or by software-controlled applications, and the device can also "communicate" with all external equipment in the form of feedback regulation.

The NO generated by means of the device according to the invention described here can be employed to stimulate the metabolism of tissues through external use in the field of dermatology for the treatment of surgical or accident-related wounds, chronic, non-healing wounds or poorly healing wounds and/or wounds infested with bacteria or fungi as well as for the treatment of dermatological diseases from the spectrum of inflammatory, immunologically regulated or autoimmune diseases. Examples of possible areas of application are:
  treatment of diabetic feet and wounds,
  treatment of neuropathic pain in cases of diabetes and other diseases,
  treatment of varicose veins,
  treatment of local superficial as well as deep ischemias and thrombopathic diseases of tissues,
  acute and chronic inflammation of the skin,
  skin allergies,
  parasitic infection of the skin,
  atopic dermatitis, especially neurodermititis,
  dermatomyositis,
  *Pemphigus vulgaris* and/or other local and systemic infections and/or acute and chronic inflammatory states,
  wound defects, such as chronic diabetic-neuropathic *Ulcus*,
  *Ulcus cruris*,
  decubitus wounds,
  infected wounds healing by second intention,
  irritation-free wounds healing by first intention, particularly such as ablative lacerations or abrasions,
  (skin) transplants, treatment of diabetic pain in the lower extremities (foot or leg); and treatment in cases of poorly perfused skin flap plastic surgeries.

Moreover, by treating larger areas of the body, it might also be possible to address systemic diseases such as, for instance, high blood pressure (hypertonia) and related hemodynamic diseases.

For purposes of treatment, the NO module is placed onto the region that is to be exposed and then exposed to the electromagnetic radiation emitted by the radiation-emitting module, preferably in direct contact or else from a certain distance. The treatment time can last between a few seconds and many hours.

In a preferred embodiment of the invention, the treatment time is between 5 and 30 minutes, preferably between 7.5 and 20 minutes and especially preferably between 10 and 15 minutes.

In one embodiment of the invention, the medical dressing is used for the treatment of diseases. Here, in an advantageous manner, the medical dressing is placed onto the part of the body that is to be exposed, that is to say, for example, onto part of the trunk or part of an extremity, and then, through the release of NO from the NO module induced by UV radiation or by a redox reaction, this particular region is exposed to the NO.

Consequently, the medical dressing according to the invention can be used not only for the treatment of chronic or acute diseases, but also for the possible prevention of such diseases. Unless otherwise indicated, the term "treatment" or "therapy" encompasses all measures for alleviating, healing or preventing the relevant diseases under discussion here.

Such a dressing treatment can be employed at intervals of 1, 2, 3, 4, 5, 6, or 7 days, or even several times daily, whereby preference is given to its use 2 to 3 times per day.

In this process, the NO module advantageously remains on the skin and, through the placement of the radiation-emitting module, the NO module can be stimulated to once again generate and release NO for a given period of time. This is made possible by a "surplus" of nitric oxide donor in the NO module, thereby allowing multiple radiation intervals.

For purposes of controlling the duration of the treatment, in a preferred manner, the medical dressing can have a time-control unit that switches off the source of radiation of the radiation-emitting module after a prescribed fixed, or preferably a flexibly programmable, period of time, thereby halting the generation of NO.

Moreover, the medical dressing can contain a dye whose color changes after a given period of time, so that the user is thereby informed about the end of the treatment.

Moreover, the medical dressing can also comprise a device for measuring the perfusion, which, on the basis of the therapy outcome, permits an excellent control of the duration and/or intensity of the treatment. The person skilled in the art is familiar with numerous devices for measuring perfusion. Examples of this are vascular tachometers or the microsensor disclosed in international patent document WO 97/46853. This sensor comprises an indicator-permeable insert that is arranged in an opening of an indicator container which is formed by a vessel, so that the insert forms a permeable wall section of the container.

Other vascular-related measuring parameters such as reddening of the skin or the skin temperature can serve as surrogate parameters for the perfusion of the skin; appropriate measuring methods and equipment for these parameters are known from the state of the art.

In another aspect, the invention puts forward a method for the treatment of a patient, comprising the following steps:

a. a medical dressing according to the invention is placed onto or adhered to the part of the body that is to be treated; and b. NO is generated and released by switching on the source of UV radiation of the radiation-emitting module.

In a preferred embodiment of this method, the treatment is selected from the group encompassing:

stimulation of the metabolism of tissues in humans and animals by means of external application;

treatment of surgical or accident-related wounds;

treatment of chronic, non-healing or poorly healing wounds;

treatment of wounds infested with bacteria and/or fungi;

treatment of dermatological diseases from the spectrum of inflammatory, immunologically regulated or autoimmune diseases;

treatment of diabetic feet and wounds;

treatment of neuropathic pain;

treatment of varicose veins;

treatment of local superficial as well as deep ischemias and thrombopathic diseases of the tissues;

treatment of acute and chronic inflammation of the skin;

treatment of skin allergies;

treatment of parasitic infections of the skin;

treatment of atopic dermatitis, especially neurodermititis, dermatomyositis and *Pemphigus vulgaris;* treatment of wound defects, such as chronic diabetic-neuropathic *Ulcus, Ulcus cruris,* decubitus wounds;

treatment of larger areas of the body for the therapy of systemic diseases such as, for example, high blood pressure (hypertonia) and related hemodynamic diseases;

treatment of patients with (skin) transplants;

treatment of diabetic pain in the lower extremities (foot or leg); and treatment in cases of poorly perfused skin flap plastic surgeries.

In a preferred embodiment, the method is employed for the treatment of chronic wounds in the lower extremities of diabetic patients.

Advantageously, the method according to the invention is characterized in that the treatment consisting of placing or adhering the medical dressing onto a part of the trunk or a part of an extremity takes place by means of UV-induced release of NO. Such a treatment can last anywhere between a few seconds and many hours.

In a preferred manner, the treatment by UV-induced NO release lasts for 5 to 30 minutes, preferably 7.5 to 20 minutes and especially preferred for 10 to 15 minutes.

In an especially preferred embodiment, the medical dressing according to the invention is used to treat chronic wounds of the lower extremities, and here especially in diabetic patients. In this context, the treatment, as a form of prophylaxis, can also reduce the risk of the occurrence of chronic wounds as well as the number of medical amputations. This goes hand in hand with a reduction in neuropathic leg pain and with the creation of an improved wound environment, translating into a noticeably improved quantity of life for the patient. Moreover, shortening the time needed for wound care means that a significant lowering of the treatment costs can be anticipated.

In one embodiment of the invention, the medical dressing is employed for the therapy of poorly healing wounds. Impaired arterial perfusion and/or venous backflow disorders are major causes for the occurrence as well as the chronicity of wounds in the lower extremities. NO-induced arterial vasodilation improves the perfusion of the affected tissue and, due to the antithrombogenic action of NO, considerably promotes or facilitates venous backflow of the blood. The NO-dependent improvement of these two hemodynamic parameters constitutes the decisive therapy-relevant aspect of a local as well as systemic effect that significantly reduces the risk of the occurrence of wounds or that considerably accelerates their healing. Consequently, the NO that is conveyed to the body in a locally limited form to the part of the extremity or to the part of the trunk that is to be treated by means of the medical dressing can be successfully employed for the therapy of poorly healing wounds.

In a special embodiment, the medical dressing according to the invention is used for the treatment of diabetic pain in the lower extremities, in other words, the foot and/or leg. Diabetic pain is a frequent occurrence over the course of diabetes. Diabetic foot or leg pain stems from prolonged elevated concentrations of glucose in the blood, which is the underlying cause of the nerve and vessel damage observed in diabetes. An NO-related arterial vasodilation improves the perfusion of the affected tissue and helps to influence the dissipation of pain with an eye towards pain reduction. Therefore, the NO that is conveyed from the outside to the foot and/or leg by the medical dressing can be utilized successfully for the therapy of diabetic foot or leg pain.

In a special embodiment of the invention, the medical dressing according to the invention is employed to treat patients with (skin) transplants, here especially for the treatment in cases of poorly perfused skin flap plastic surgery. The two above-mentioned hemodynamic parameters, namely, arterial perfusion and venous backflow, constitute essential parameters for the therapeutic success in cases of skin flap plastic surgery. The expression skin flap plastic surgery refers to techniques in plastic surgery that graft skin and/or tissue from a (dispensable) site to a new, desired site in the same individual. As a rule, these are purely skin flaps, although any tissue, with or without skin, can be transplanted with a pedicle (in other words, along with its appertaining blood-supplying vessels and nerves) or they can be transplanted free (that is to say, involving a connection of the blood vessels to the source of blood of the new location). The functional acceptance of the transplanted tissue here is exclusively dependent on the arterial blood supply as well as on a regulated venous drainage. NO-induced arterial vasodilation improves perfusion and thus the requisite supply in cases of skin flap plastic surgery, while the antithrombogenic effect of NO promotes and facilitates venous drainage or backflow of the blood. Therefore, NO preparations used from the outside can ensure or promote the success of a therapy option based on skin flap plastic surgery.

In one special aspect, the invention puts forward the following embodiments:

Embodiment 1

Using the emission of electromagnetic radiation from one of the modules (hereinafter referred to as a radiation-emitting module), a device that has any desired dimension and surface area and that is made up of at least two modules can cleave, preferably photolytically cleave, photolabile or redox-labile nitric oxide donors (hereinafter referred to as NOD=NO derivatives) that are contained in a preferably closely adjoining second module (hereinafter referred to as an NO module), so that nitric oxide (NO) can be generated in the NO module and can preferably be released from the NO module.

Embodiment 2

The device according to Embodiment 1, characterized in that the NO module is preferably an integral component of the entire device that is permanently joined to the radiation-emitting module, but also encompassing the possibility that the radiation-emitting module and the NO module can be physically separated from each other so that the radiation of the NO module does not take place in directly applied contact with the radiation-emitting module but rather at a certain distance from it.

Embodiment 3

The device according to Embodiments 1 and 2, characterized in that, for an optimal cleavage of the photolabile NO donors that are incorporated in the NO module, the radiation-emitting module can emit electromagnetic radiation at wavelengths that, alone or with the assistance of chemical, physical or biological methods, can induce a cleavage of nitric oxide donors and thus a release of nitric oxide, whereby, through the presence of additional substances with catalytic properties or specific light-acceptor properties, the NO generation is facilitated or even made possible in the first place (for example, with the help of transition metals such as, for instance, Cu' ions, chromophores and other substances with which, for example, even electromagnetic radiation that is outside of the UVA spectrum can be capable of enabling the release of NO from the appertaining NO-forming agents).

Embodiment 4

The device according to Embodiments 1 to 3, characterized in that the source of electromagnetic radiation that is integrated into the radiation-emitting module can be a glow-discharge lamp or a gas discharge lamp (low-pressure-discharging or high-pressure-discharging) coated with appropriate fluorochromes, light-emitting diodes (LED), organic light-emitting diodes (OLED), lasers or any other electromagnetic source of radiation that is capable of generating NO from the appertaining chemical precursors or substrates.

Embodiment 5

The device according to Embodiments 1 to 4, characterized in that, along with an electronic control unit for the light source, the source of electromagnetic radiation of the radiation-emitting module can be installed in a part or in a housing in a compact manner, or else it can be physically separated from this control unit and only connected via a wired connection, or else it can even be completely separated, whereby in this case, the light source can be controlled remotely by the control unit.

Embodiment 6

The device according to Embodiments 1 to 5, characterized in that the NO generation in or from the NO module is subject to electronically regulated safety management that 1) is preferably regulated through the manipulation of various technical, physical or chemical setting parameters on the radiation-emitting module or else on the NO module,
2) has a safety-relevant and treatment-relevant sensor system (for example, for NO, $NO_2$, temperature, light intensity, skin reddening, time switch-OFF, etc.),
3) has joining and connection possibilities to external equipment (for instance, computers, smart phones, etc.) and can be controlled remotely and actuated by software-controlled applications, whereby a user-specific and electronically controlled recognition and utilization acceptance of the NO module that is specifically loaded with nitric oxide donors or their replaceable or exchangeable and photolabile NO derivatives constitute an essential part of the safety management of the device.

Embodiment 7

The device according to Embodiments 1 to 6, characterized in that it can be employed to stimulate the metabolism of tissues through external use in the field of dermatology and surgery for the treatment of surgical or accident-related wounds, chronic, non-healing wounds or poorly healing wounds and/or wounds infested with bacteria and/or fungi as well as for the treatment of dermatological diseases from the spectrum of inflammatory, immunologically regulated or autoimmune diseases, for instance, in the treatment of diabetic feet and wounds, neuropathic pain in diabetic patients as well as other diseases, of varicose veins, local superficial as well as deep ischemias and thrombopathic diseases of tissues, acute and chronic inflammation of the skin, skin allergies, parasitic infections of the skin, atopic dermatitis, especially neurodermititis, dermatomyositis, *Pemphigus vulgaris* and/or other local and systemic infections and/or acute and chronic inflammatory states, wound defects, such as chronic diabetic-neuropathic *Ulcus, Ulcus cruris*, decubitus wounds, infected wounds healing by second intention, irritation-free wounds healing by first intention, particularly such as ablative lacerations or abrasions, (skin) transplants but also for the treatment of larger areas of the body in the therapy of systemic diseases such as, for instance, high blood pressure (hypertonia) and related hemodynamic diseases, whereby such a treatment can individually last between a few seconds and many hours, whereby, for purposes of a treatment, the NO module is placed onto the region that is to be exposed and exposed to the electromagnetic radiation emitted by the radiation-emitting module, preferably in direct contact or else from a certain distance, whereby such a treatment can last between a few seconds and many hours.

LIST OF REFERENCE NUMERALS 1 inner layer
2 middle layer
3 outer layer
4 backing layer
5 transparent window in the backing layer
6 fastening means for the radiation-emitting module
7 non-adhesive part of an inner layer
8 cavity in the inner area of the dressing
9 source of radiation
10, 10' spacers

FIGURES

Figure 2:
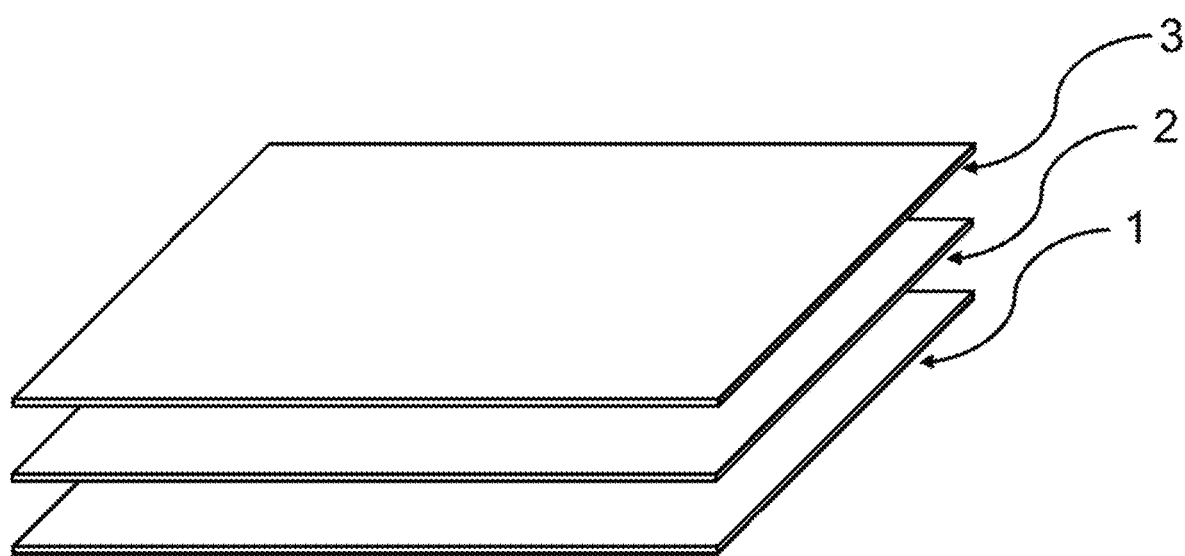
Figure 3:
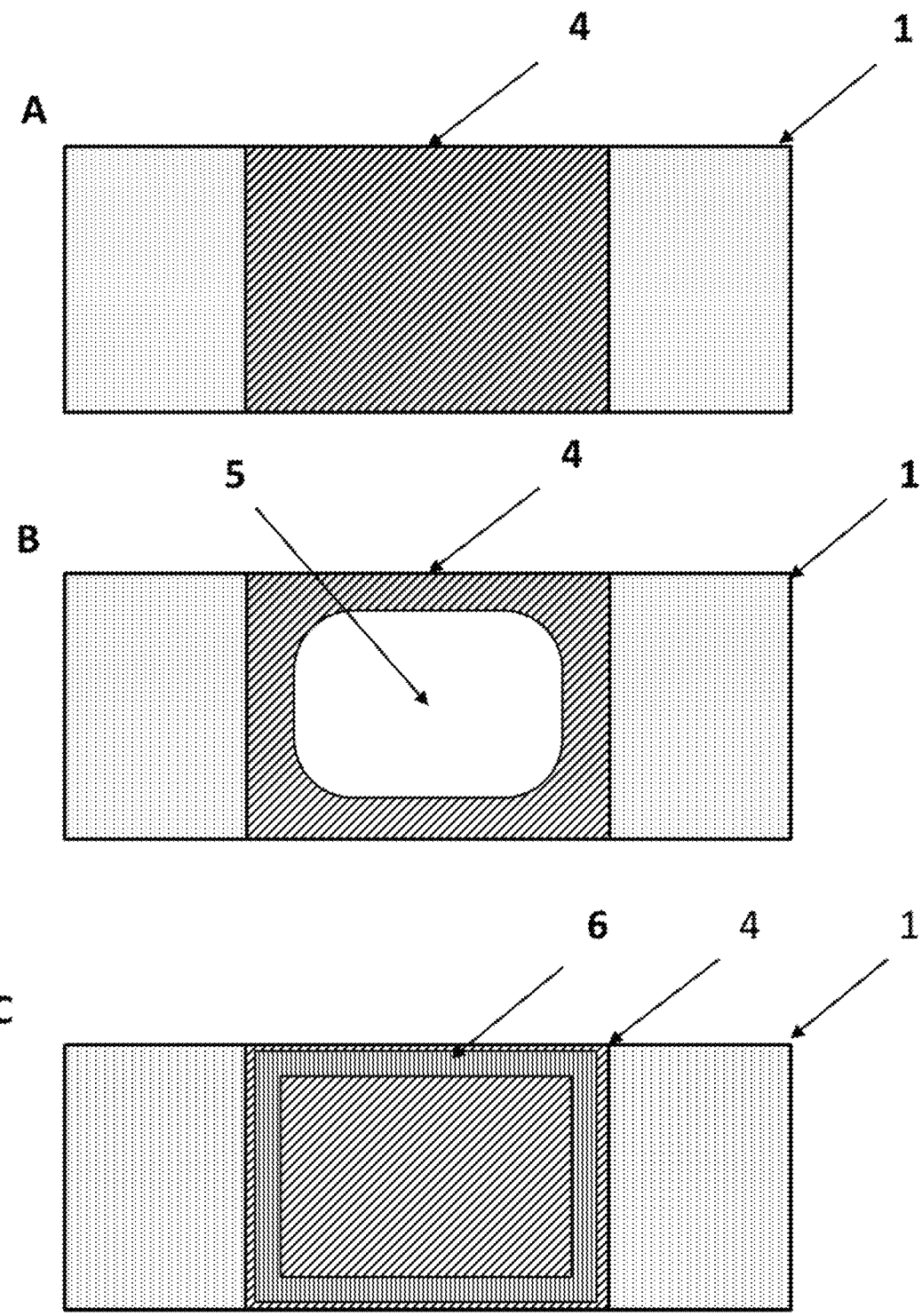
Figure 4:
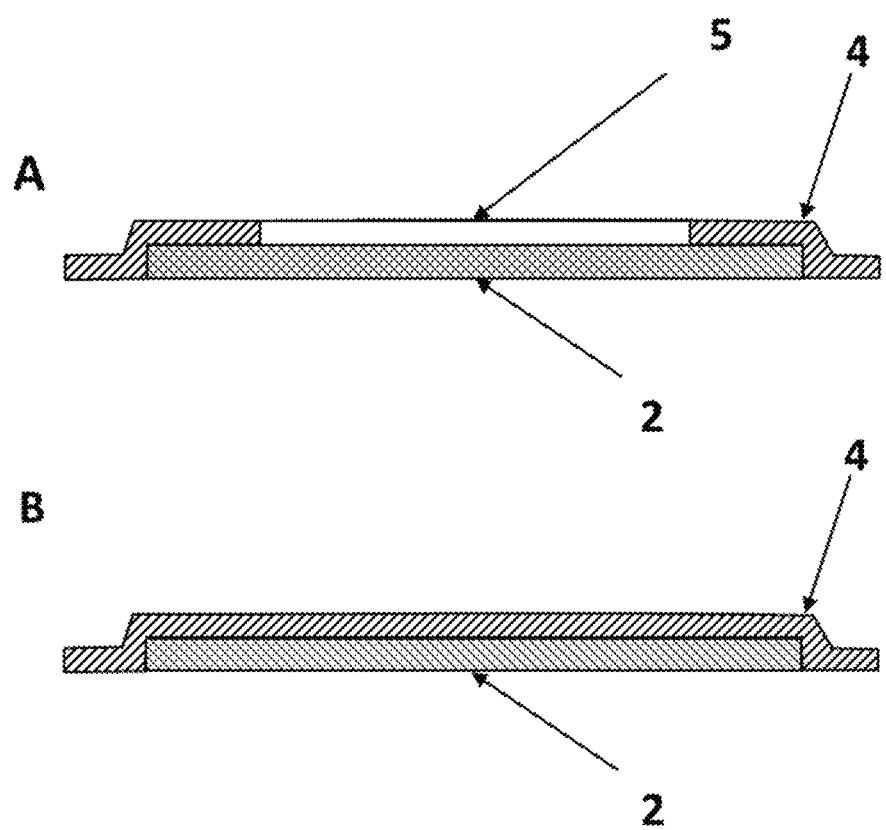
Figure 5:
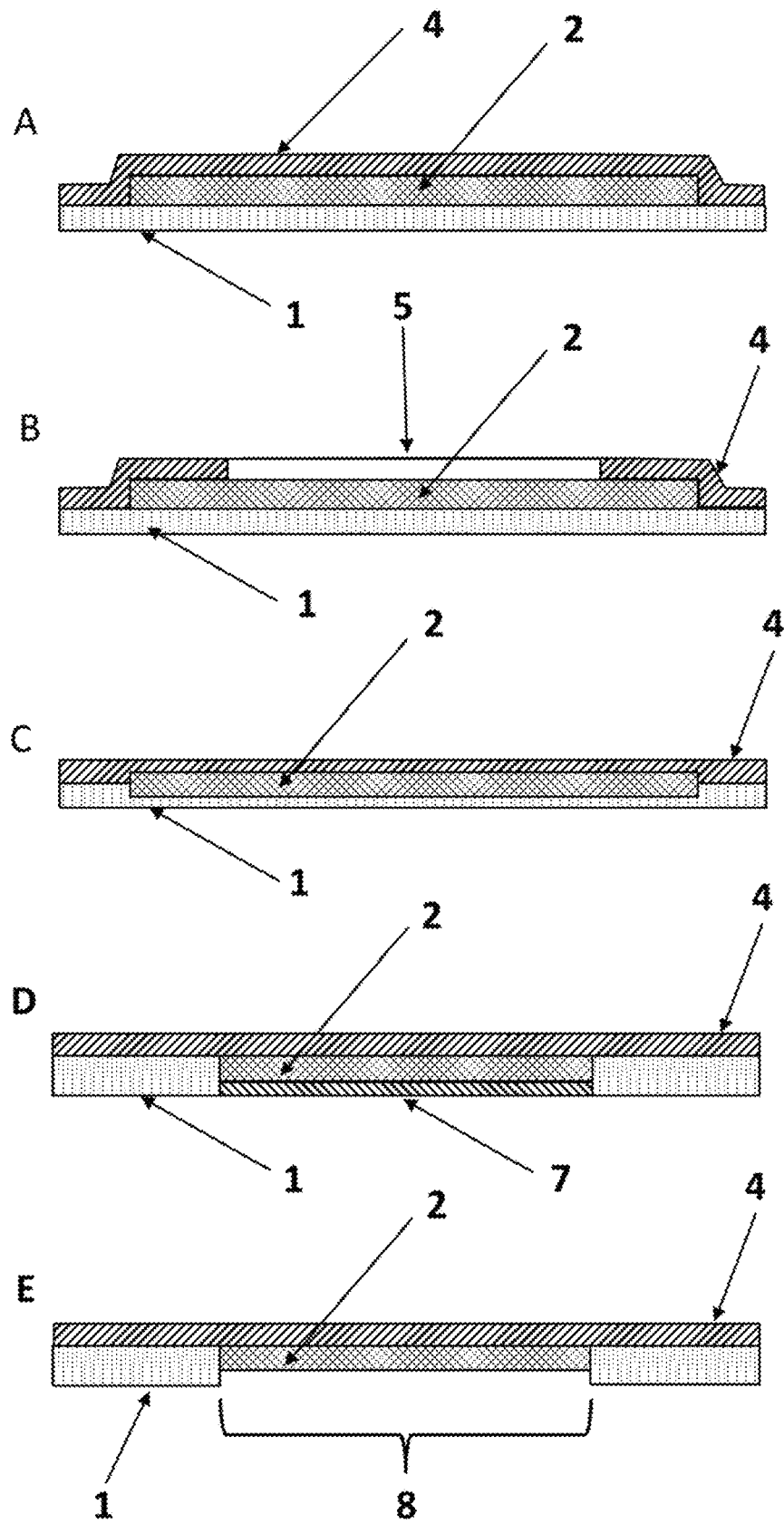
Figure 6:
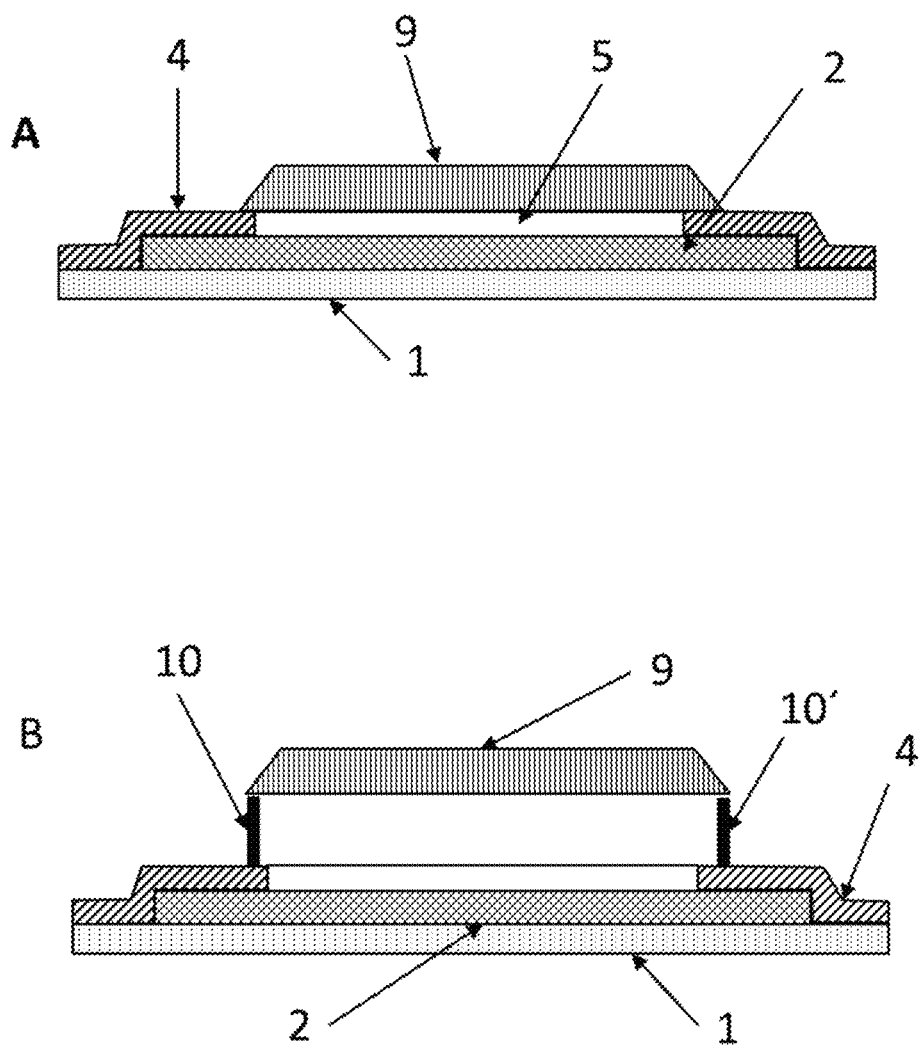

The invention will be described in greater detail bellow on the basis of the figures, without this constituting a restriction of the invention. The following is shown:

FIG. 1: the application for wound treatment in which the NO module is placed as a flexible dressing onto the leg wound and UV radiation is administered by means of a radiation-emitting module placed above it, so that the NO module releases NO on the side facing the body;

FIG. 2: a schematic exploded view of an embodiment of the NO module of the medical dressing having an inner layer (1), a middle layer (2) and an outer layer (3);

FIG. 3: a schematic view of a multi-layered NO module in a top view with the inner layer (1) and the backing layer (4) in (A), with an additional transparent area as the activation window in (B), and a fastening means (for example, in the form of a Velcro fastener) for the radiation-emitting module in (C);

FIG. 4: a schematic view of a two-layered NO module in a cross sectional view with the middle layer (2) and the backing layer (4) in (B), with an additional transparent area as the activation window in (A);

FIG. 5: a schematic view of a three-layered NO module in a cross sectional view with the inner layer (1), the middle layer (2) and the backing layer (4) in (A), with an additional transparent area as the activation window in (B), with a flat incorporated inner layer in (C), with an inner layer that is non-adhesive in the area of the middle layer in (D), and with a cavity that is closed on all sides below the middle layer in (E);

FIG. 6: a schematic view of the medical dressing in a cross section with a three-layered NO module with the inner layer (1), the middle layer (2) and the backing layer (4) with a transparent activation window (5) and with the superimposed radiation source in the form of a radiation-emitting module in (A), with additional spacers (10, 10') in (B).

LITERATURE

[1] K. D. Kröncke, K. Fehsel, and V. Kolb-Bachofen, Inducible nitric oxide synthase in human diseases. *Clin Exp Immunol* 113 (1998) 147-56.
[2] K. Matsunaga, and R. F. Furchgott, Responses of rabbit aorta to nitric oxide and superoxide generated by ultraviolet irradiation of solutions containing inorganic nitrite. *J Pharmacol Exp Ther* 259 (1991) 1140-6.
[3] M. Fischer, and P. Warneck, Photodecomposition of nitrite and undissociated nitrous acid in aqueous solution. *J. Phys. Chem.* 100 (1996) 18749-18756.
[4] H. Strehlow, and I. Wagner, Flash photolysis in aqueous nitrite solutions. *Z. Phys. Chem. NF* 132 (1982) 151-160.
[5] S. Frank, H. Kampfer, C. Wetzler, and J. Pfeilschifter, Nitric oxide drives skin repair: novel functions of an established mediator. *Kidney Int* 61 (2002) 882-8.
[6] S. Frank, B. Stallmeyer, H. Kampfer, N. Kolb, and J. Pfeilschifter, Nitric oxide triggers enhanced induction of vascular endothelial growth factor expression in cultured keratinocytes (HaCaT) and during cutaneous wound repair. *Faseb J* 13 (1999) 2002-14.
[7] S. Frank, H. Kampfer, M. Podda, R. Kaufmann, and J. Pfeilschifter, Identification of copper/zinc superoxide dismutase as a nitric oxide-regulated gene in human (HaCaT) keratinocytes: implications for keratinocyte proliferation. *Biochem J* 346 Pt 3 (2000) 719-28.
[8] K. Yamasaki, H. D. Edington, C. McClosky, E. Tzeng, A. Lizonova, I. Kovesdi, D. L. Steed, and T. R. Billiar, Reversal of impaired wound repair in iNOS-deficient mice by topical adenoviral-mediated iNOS gene transfer. *J Clin Invest* 101 (1998) 967-71.
[9] J. Pfeilschifter, W. Eberhardt, and A. Huwiler, Nitric oxide and mechanisms of redox signalling: matrix and matrix-metabolizing enzymes as prime nitric oxide targets. *Eur J Pharmacol* 429 (2001) 279-86.
[10] Y. Ishii, T. Ogura, M. Tatemichi, H. Fujisawa, F. Otsuka, and H. Esumi, Induction of matrix metalloproteinase gene transcription by nitric oxide and mechanisms of MMP-1 gene induction in human melanoma cell lines. *Int J Cancer* 103 (2003) 161-8.
[11] M. B. Witte, F. J. Thornton, D. T. Efron, and A. Barbul, Enhancement of fibroblast collagen synthesis by nitric oxide. *Nitric Oxide* 4 (2000) 572-82.
[12] F. Verrecchia, and A. Mauviel, TGF-beta and TNF-alpha: antagonistic cytokines controlling type I collagen gene expression. *Cell Signal* 16 (2004) 873-80.
[13] D. A. Siwik, and W. S. Colucci, Regulation of matrix metalloproteinases by cytokines and reactive oxygen/nitrogen species in the myocardium. *Heart Fail Rev* 9 (2004) 43-51.
[14] V. M. Darley-Usmar, R. P. Patel, V. B. O'Donnell, and B. A. Freeman, Antioxidant actions of nitric oxide. in: L. J. Ignarro, (Ed.), Nitric Oxide: Biology and Pathobiology, Academic Press, San Diego, (2000), pp. 265-276.
[15] S. P. Goss, B. Kalyanaraman, and N. Hogg, Antioxidant effects of nitric oxide and nitric oxide donor compounds on low-density lipoprotein oxidation. *Methods Enzymol* 301 (1999) 444-53.
[16] D. A. Wink, J. A. Cook, R. Pacelli, J. Liebmann, M. C. Krishna, and J. B. Mitchell, Nitric oxide (NO) protects against cellular damage by reactive oxygen species. *Toxicol Lett* 82-83 (1995) 221-6.
[17] B. Brüne, A. von Knethen, and K. B. Sandau, Nitric oxide (NO): an effector of apoptosis. *Cell Death Differ* 6 (1999) 969-75.
[18] D. Moellering, J. McAndrew, R. P. Patel, T. Cornwell, T. Lincoln, X. Cao, J. L. Messina, H. J. Forman, H. Jo, and V. M. Darley-Usmar, Nitric oxide-dependent induction of glutathione synthesis through increased expression of gamma-glutamylcysteine synthetase. *Arch Biochem Biophys* 358 (1998) 74-82.
[19] U. Forstermann, M. Nakane, W. R. Tracey, and J. S. Pollock, Isoforms of nitric oxide synthase: functions in the cardiovascular system. *Eur Heart J* 14 Suppl I (1993) 10-5.
[20] P. He, M. Zeng, and F. E. Curry, Effect of nitric oxide synthase inhibitors on basal microvessel permeability and endothelial cell [Ca2+]i. *Am J Physiol* 273 (1997) H747-55.
[21] M. Toborek, and S. Kaiser, Endothelial cell functions. Relationship to atherogenesis. *Basic Res Cardiol* 94 (1999) 295-314.
[22] M. Kelm, and B. Strauer, Endotheliale Dysfunktion; Therapeutische and prognostische Relevanz [Endothelial dysfunction; therapeutic and prognostic relevance]. *Internist.* 40 (1999) 1300-1307.
[23] T. P. Amadeu, A. B. Seabra, M. G. de Oliveira, and A. M. Costa, S-nitrosoglutathione-containing hydrogel accelerates rat cutaneous wound repair. *J Eur Acad Dermatol Venereol* 21 (2007) 629-37.
[24] R. Weller, and M. J. Finnen, The effects of topical treatment with acidified nitrite on wound healing in normal and diabetic mice. *Nitric Oxide* 15 (2006) 395-9.
[25] A. B. Shekhter, V. A. Serezhenkov, T. G. Rudenko, A. V. Pekshev, and A. F. Vanin, Beneficial effect of gaseous nitric oxide on the healing of skin wounds. *Nitric Oxide* 12 (2005) 210-9.
[26] W. S. McDonald, T. P. Lo, Jr., M. Thurmond, C. Jones, R. Cohen, A. Miller, and D. Beasley, Role of nitric oxide in skin flap delay. *Plast Reconstr Surg* 113 (2004) 927-31.
[27] C. Belge, P. B. Massion, M. Pelat, and J. L. Balligand, Nitric oxide and the heart: update on new paradigms. *Ann NY Acad Sci* 1047 (2005) 173-82.
[28] B. Gaston, Summary: systemic effects of inhaled nitric oxide. *Proc Am Thorac Soc* 3 (2006) 170-2.
[29] T. M. Dawson, and S. H. Snyder, Gases as biological messengers: nitric oxide and carbon monoxide in the brain. *J Neurosci* 14 (1994) 5147-59.
[30] C. C. Miller, M. K. Miller, A. Ghaffari, and B. Kunimoto, Treatment of chronic nonhealing leg ulceration with gaseous nitric oxide: a case study. *J Cutan Med Surg* 8 (2004) 233-8.
[31] A. Ghaffari, D. H. Neil, A. Ardakani, J. Road, A. Ghahary, and C. C. Miller, A direct nitric oxide gas delivery system for bacterial and mammalian cell cultures. *Nitric Oxide* 12 (2005) 129-40.
[32] A. Ghaffari, C. C. Miller, B. McMullin, and A. Ghahary, Potential application of gaseous nitric oxide as a topical antimicrobial agent. *Nitric Oxide* 14 (2006) 21-9.
[33] A. Ghaffari, R. Jalili, M. Ghaffari, C. Miller, and A. Ghahary, Efficacy of gaseous nitric oxide in the treatment of skin and soft tissue infections. *Wound Repair Regen* 15 (2007) 368-77.
[34] Z. S. Galis, and J. J. Khatri, Matrix metalloproteinases in vascular remodeling and atherogenesis: the good, the bad, and the ugly. *Circ Res* 90 (2002) 251-62.
[35] S. C. Tyagi, and M. R. Hayden, Role of nitric oxide in matrix remodeling in diabetes and heart failure. *Heart Fail Rev* 8 (2003) 23-8.
[36] J. Pfeilschifter, W. Eberhardt, and K. F. Beck, Regulation of gene expression by nitric oxide. *Pflugers Arch* 442 (2001) 479-86.
[37] R. Zamora, Y. Vodovotz, K. S. Aulak, P. K. Kim, J. M. Kane, 3rd, L. Alarcon, D J. Stuehr, and T. R. Billiar, A DNA microarray study of nitric oxide-induced genes in mouse hepatocytes: implications for hepatic heme oxygenase-1 expression in ischemia/reperfusion. *Nitric Oxide* 7 (2002) 165-86.
[38] J. Hemish, N. Nakaya, V. Mittal, and G. Enikolopov, Nitric oxide activates diverse signaling pathways to regulate gene expression. *J Biol Chem* 278 (2003) 42321-9.
[39] M. Ziche, L. Morbidelli, E. Masini, S. Amerini, H. J. Granger, C. A. Maggi, P. Geppetti, and F. Ledda, Nitric oxide mediates angiogenesis in vivo and endothelial cell growth and migration in vitro promoted by substance P. *J Clin Invest* 94 (1994) 2036-44.
[40] S. J. Leibovich, P. J. Polverini, T. W. Fong, L. A. Harlow, and A. E. Koch, Production of angiogenic activity by human monocytes requires an L-arginine/nitric oxide-synthase-dependent effector mechanism. *Proc Natl Acad Sci USA* 91 (1994) 4190-4.
[41] N. S. Bryan, B. O. Fernandez, S. M. Bauer, M. F. Garcia-Saura, A. B. Milsom, T. Rassaf, R. E. Maloney, A. Bharti, J. Rodriguez, and M. Feelisch, Nitrite is a signaling molecule and regulator of gene expression in mammalian tissues. *Nature Chemical Biology* 1 (2005) 290-297.

The invention claimed is:
1. A medical dressing comprising:
a nitric oxide module containing one or more photolabile nitric oxide donors;
a radiation-emitting module including a source of radiation, said radiation-emitting module being configured such that electromagnetic radiation emitted from the source cleaves the nitric oxide donors in the nitric oxide module and thereby generates nitric oxide for release from the nitric oxide module; and a radical trapping system configured to degrade or neutralize one or more reactive intermediate products of light-induced nitric oxide donor decomposition selected from the group consisting of polyoxidized nitrogen oxides, oxygen radical anions, hydrated electrons and hydroxyl radicals;

wherein the medical dressing comprises an outer layer, a middle layer and an inner layer, wherein the outer layer is impermeable for nitric oxide, wherein the one or more photolabile nitric oxide donors are present in the middle layer, and wherein the radical trapping system is present in the inner layer.

2. The medical dressing according to claim 1, further comprising transition metal cations.

3. The medical dressing according to claim 2, wherein the transition metal cations are $Cu^{2+}$ ions.

4. The medical dressing according to claim 1, wherein the electromagnetic radiation emitted from the radiation-emitting module has a wavelength ranging from 400 nm to 470 nm.

5. The medical dressing according to claim 1, wherein the radical trapping system is selected from the group consisting of:
   ascorbic acid;
   ascorbate;
   vitamin E
   derivatives of vitamin E
   thiols
   radical traps;
   enzymes that break down oxygen species; and
   enzymes that break down nitrogen species.

6. The medical dressing according to claim 1, wherein the medical dressing is a medical wound dressing.

7. The medical dressing according to claim 1, wherein the nitric oxide module is permanently joined to the radiation-emitting module.

8. The medical dressing according to claim 1, wherein the nitric oxide module is arranged a predetermined distance away from the radiation-emitting module.

9. The medical dressing according to claim 1, wherein the nitric oxide module is configured in the form of a replaceable and disposable article.

10. The medical dressing according to claim 1, wherein the source of electromagnetic radiation of the radiation-emitting module is installed in a housing together with an electronic control unit for the electromagnetic radiation source.

11. The medical dressing according to claim 1, wherein the source of electromagnetic radiation of the radiation-emitting module is physically separated from an electronic control unit for the source of electromagnetic radiation, and wherein control is carried out via a wired connection or by a remote wireless connection.

12. The medical dressing according to claim 1, wherein the source of electromagnetic radiation is selected from the group comprising a glow-discharge or gas-discharge lamp (low-pressure discharging or high-pressure discharging) coated with appropriate fluorochromes, a light-emitting diode (LED), an organic light-emitting diode (OLED) and a laser.

13. The medical dressing according to claim 1, wherein the one or more photolabile nitric oxide donors is selected from the group consisting of organic nitrates, inorganic nitrates, nitrites, sulfur-nitroso compounds, nitrogen-nitroso compounds, oxygen-nitroso compounds, NO-metal compounds and NO-chelating substances.

14. The medical dressing according to claim 1, wherein the one or more photolabile nitric oxide donors is an inorganic nitrite.

15. The medical dressing according to claim 1, wherein the one or more photolabile nitric oxide donors is selected from the group consisting of $LiNO_2$, $NaNO_2$, $KNO_2$, $RbNO_2$, $CsNO_2$, $FrNO_2$, $Be(NO_2)_2$, $Mg(NO_2)_2$, $Ca(NO_2)_2$, $Sr(NO_2)_2$, $Ba(NO_2)_2$ and $Ra(NO_2)_2$.

16. The medical dressing according to claim 1, wherein the photolabile nitric oxide donors includes $NaNO_2$ and the radical trapping system includes ascorbic acid or ascorbate.

17. The medical dressing according to claim 1, further comprising a safety-relevant and treatment-relevant sensor system.

18. The medical dressing according to claim 17, wherein the safety-relevant and treatment-relevant sensor system is for NO, $NO_2$, temperature, light intensity, skin reddening, or time switch-OFF.

19. A method for treatment of a human body comprising placing or adhering a medical dressing according to claim 1 onto a region that is to be treated.

20. The method according to claim 19, wherein the treatment is selected from the group comprising:
   treatment of diabetic feet and wounds;
   treatment of neuropathic pain;
   treatment of varicose veins;
   treatment of local superficial as well as deep ischemias and thrombopathic diseases of tissues;
   treatment of acute and chronic inflammation of skin;
   treatment of skin allergies;
   treatment of parasitic infections of skin;
   treatment of atopic dermatitis;
   treatment of wound defects;
   treatment of infected wounds healing by second intention;
   treatment of wounds healing by first intention;
   treatment of high blood pressure (hypertonia) and related hemodynamic diseases;
   treatment of patients with skin transplants;
   treatment of diabetic pain in lower extremities; and
   treatment in cases of poorly perfused skin flap plastic surgeries.

21. The method according to claim 19, wherein the treatment is for chronic wounds in lower extremities of diabetic patients.

22. The method according to claim 19, wherein the treatment lasts for a period between 5 and 30 minutes.

* * * * *